(12) United States Patent
Webster et al.

(10) Patent No.: US 9,714,446 B2
(45) Date of Patent: Jul. 25, 2017

(54) COMPOSITIONS AND METHODS FOR THE DETECTION OF SMALL RNAS

(75) Inventors: Philippa J. Webster, Seattle, WA (US); Lucas M. Dennis, Seattle, WA (US); Richard K. Boykin, Shoreline, WA (US)

(73) Assignee: NanoString Technologies, Inc., Seattle, WA (US)

( * ) Notice: Subject to any disclaimer, the term of this patent is extended or adjusted under 35 U.S.C. 154(b) by 415 days.

(21) Appl. No.: 13/025,458

(22) Filed: Feb. 11, 2011

(65) Prior Publication Data

US 2011/0201515 A1 Aug. 18, 2011

Related U.S. Application Data

(60) Provisional application No. 61/303,517, filed on Feb. 11, 2010.

(51) Int. Cl.
C12Q 1/68 (2006.01)

(52) U.S. Cl.
CPC ......... C12Q 1/6809 (2013.01); C12Q 1/6816 (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,835,263 A | 5/1989 | Nguyen et al. |
| 5,270,184 A | 12/1993 | Walker et al. |
| 5,320,814 A | 6/1994 | Walt et al. |
| 5,334,711 A | 8/1994 | Sproat et al. |
| 5,399,491 A | 3/1995 | Kacian et al. |
| 5,422,252 A | 6/1995 | Walker et al. |
| 5,527,675 A | 6/1996 | Coull et al. |
| 5,539,082 A | 7/1996 | Nielsen et al. |
| 5,543,838 A | 8/1996 | Hosier et al. |
| 5,623,049 A | 4/1997 | L obberding et al. |
| 5,714,331 A | 2/1998 | Buchardt et al. |
| 5,801,115 A | 9/1998 | Albers et al. |
| 6,001,311 A | 12/1999 | Brennan |
| 6,027,923 A | 2/2000 | Wallace |
| 6,207,392 B1 | 3/2001 | Weiss et al. |
| 6,300,074 B1 | 10/2001 | Gold et al. |
| 6,355,431 B1 | 3/2002 | Chee et al. |
| 6,429,027 B1 | 8/2002 | Chee et al. |
| 6,942,968 B1 | 9/2005 | Dickinson et al. |
| 9,046,477 B2 | 6/2015 | Empedocles et al. |
| 9,228,948 B2 | 1/2016 | Empedocles et al. |
| 9,297,762 B2 | 3/2016 | Empedocles et al. |
| 9,304,084 B2 | 4/2016 | Empedocles et al. |
| 2001/0002315 A1 | 5/2001 | Schultz et al. |
| 2001/0007775 A1 | 7/2001 | Seul et al. |
| 2001/0023078 A1 | 9/2001 | Bawendi et al. |
| 2001/0029049 A1 | 10/2001 | Walt et al. |
| 2001/0034034 A1 | 10/2001 | Bruchez et al. |
| 2001/0053334 A1 | 12/2001 | Chen et al. |
| 2002/0028457 A1 | 3/2002 | Empedocles et al. |
| 2002/0034737 A1 | 3/2002 | Drmanac |
| 2002/0034827 A1 | 3/2002 | Singh et al. |
| 2002/0039728 A1 | 4/2002 | Kain et al. |
| 2002/0051971 A1 | 5/2002 | Stuelpnagel et al. |
| 2002/0068018 A1 | 6/2002 | Pepper et al. |
| 2002/0177141 A1 | 11/2002 | Chee et al. |
| 2002/0187515 A1 | 12/2002 | Chee et al. |
| 2003/0008323 A1 | 1/2003 | Ravkin et al. |
| 2003/0028981 A1 | 2/2003 | Chandler et al. |
| 2003/0186426 A1 | 10/2003 | Brewer et al. |
| 2005/0233318 A1 | 10/2005 | Chee et al. |
| 2006/0019258 A1 | 1/2006 | Yeakley |
| 2007/0178476 A1 | 8/2007 | Shima et al. |
| 2009/0181390 A1 | 7/2009 | Li et al. |

FOREIGN PATENT DOCUMENTS

| | | | | |
|---|---|---|---|---|
| WO | WO-8902439 A1 | 3/1989 | | |
| WO | WO-9103162 A1 | 3/1991 | | |
| WO | WO-9207065 A1 | 4/1992 | | |
| WO | WO-9315187 A1 | 8/1993 | | |
| WO | WO-9426934 A2 | 11/1994 | | |
| WO | WO-9506734 A1 | 3/1995 | | |
| WO | WO-9511910 A1 | 5/1995 | | |
| WO | WO-9604000 A1 | 2/1996 | | |
| WO | WO-9707245 | 2/1997 | | |
| WO | WO-9714028 | 4/1997 | | |
| WO | WO-9918434 | 4/1999 | | |
| WO | WO-9954459 A2 | 10/1999 | | |
| WO | WO-0073777 | 12/2000 | | |
| WO | WO-0100875 | 1/2001 | | |
| WO | WO 2005/118806 | * 12/2005 | ............. | C12N 15/09 |
| WO | WO 2005/118806 A2 | 12/2005 | | |
| WO | WO 2007/076128 | * 7/2007 | ............... | C12Q 1/68 |
| WO | WO-2007076128 A2 | 7/2007 | | |
| WO | WO-2008124847 A2 | 10/2008 | | |
| WO | WO-2009029742 A1 | 3/2009 | | |
| WO | WO-2009101193 A1 | 8/2009 | | |

OTHER PUBLICATIONS

Wang et al in "Direct and sensitive miRNA profiling from low-input total RNA" (RNA, 2007, vol. 13, pp. 151-159).*
Chang et al 2008.*
Maroney et al in A rapid, quantitative assay for direct detection of microRNAs and other small RNAs using splinted ligation (RNA, vol. 13, No. 6, pp. 930-936; Apr. 2007; IDS reference).*
Maroney et al in A rapid, quantitative assay for direct detection of microRNAs and other small RNAs using splinted ligation (RNA, vol. 13, No. 6, pp. 930-936; Apr. 2007.*
Maroney et al. "A Rapid, Quantitative Assay for Direct Detection of microRNAs and Other Small RNAs Using Splinted Ligation." *RNA*. 13.6(2007):930-936.
Allawi et al., "Thermodynamics and NMR of Internal G-T Mismatches in DNA", *Biochemistr*, 36: 10581-10594 (1997).

(Continued)

*Primary Examiner* — Catherine S Hibbert
(74) *Attorney, Agent, or Firm* — Cooley LLP; Ivor R. Elrifi; Matthew Pavao

(57) ABSTRACT

The invention provides compositions and methods for the detection of small RNA molecules in a multiplexed reaction. The assays and kits described herein are applicable for the identification, diagnosing, and monitoring of disorders including, but not limited to cancer, developmental and degenerative disease, neurological disorders, and stem cell disorders.

15 Claims, 11 Drawing Sheets

(56) References Cited

OTHER PUBLICATIONS

Altschul et al., "Basic Local Alignment Search Tool", *J. Mol. Biol.*, 215:403-410 (1990).
Altschul et al., "Gapped BLAST and PSI-BLAST: A New Generation of Protein Database Search Programs", *Nucleic Acids Res.*, 25(17):3389-3402 (1997).
Brennan et al., "Two-Dimensional Parallel Array Technology as a New Approach to Automated Combinatorial Solid-Phase Organic Synthesis", *Biotechnol Bioeng.*, 61:33-45 (1998).
Caruthers et al., "Chemical Synthesis of Deoxyoligonucleotides and Deoxyoligonucleotide Analogs", *Methods in Enzymology*, 211:3-19 (1992).
Cload et al., "Polyether Tethered Oligonucleotide Probes", *J. Am. Chem. Soc.*, 113(16): 63246326 (1991).
Corey, "Peptide Nucleic Acids: Expanding the Scope of Nucleic Acid Recognition", *Trends Biotechnol.*, 15(6): 224-229 (1997).
Devereux et al. "A Comprehensive Set of Sequence Analysis Programs for the VAX", *Nucleic Acids Res.*, 12(1):387 (1984).
Dufresne et al., "Patent Searches for Genetic Sequences: How to Retrieve Relevant Records from Patented Sequence Databases", *Nat Biotechnol*, 20(12): 1269-71 (2002).
Durand et al., "Circular Dichroism Studies of an Oligodeoxyribonucleotide Containing a Hairpin Loop Made of a Hexaethylene Glycol Chain: Conformation and Stability", *Nucleic Acids Res.*, 18: 6353 (1990).
Ferentz et al. "Disulfide-Crosslinked Oligonucleotides", *J. Am. Chem. Soc.*, 113: 4000 (1991).
Geiss et al., "Direct Multiplexed Measurement of Gene Expression With Color-Coded Probe Pairs", *Nature Biotechnolog*, 26(3): 317-325 (2008).
Guatelli et al., "Isothermal, In Vitro Amplification of Nucleic Acids by a Multienzyme Reaction Modeled After Retroviral Replication" *Proc. Natl. Acad. Sci. USA*, 87: 1874 (1990).
Hunziker et al., "Nucleic Acid Analogues: Synthesis and Properties", *Modern Synthetic Methods*, 331-417 (1995).
Hyrup et al., "Peptide Nucleic Acids (PNA): Synthesis, Properties and Potential Applications", *Bioorg Med Chem.*, 4(1): 5-23 (1996).
Jaschke et al. "Automated Incorporation of Polyethylene Glycol into Synthetic Oligonucleotides", *Tetrahedron Lett.*, 34: 301 (1993).
Kumar et al., "Pyrrolidine Nucleic Acids: DNA/PNA Oligomers with 2-Hydroxy/Aminomethyl-4-(thymin-1-yl)pyrrolidine-N-acetic acid", *Organic Letters*, 3(9): 1269-1272 (2001).
Lagriffoul et al., "The Synthesis, Co-Oligomerization and Hybridization of a Thymine-Thymine Heterodimer Containing PNA", *Bioorganic & Medicinal Chemistry Letters*, 4(8): 1081-1082 (1994).
Landegren et al., "A Ligase-Mediated Gene Detection Technique", *Science*, 241:1077 (1988).
Ma et al., "Design and Synthesis of RNA Miniduplexes Via a Synthetic Linker Approach", *Nucleic Acids Res.*, 21:2585-2589 (1993).
Ma et al., "Design and Synthesis of RNA Miniduplexes Via a Synthetic Linker Approach", *Biochemistry*, 32: 1751 (1993).
McCurdy et al., "Deoxyligonucleotides with Inverted Polarity Synthesis and Use in Triple-Helix Formation", *Nucleosides & Nucleotides*, 10: 287 (1991).
Mesmaeker et al., "Novel Backbone Replacements for Oligonucleotides, in Carbohydrate Modifications in Antisense Research", *ACS* 580: 24-39 (1994).
Myers et al., "Optimal Alignments in Linear Space", *CABIOS*, 4(1):11-17 (1988).
Needleman et al., "A General Method Applicable to the Search for Similarities in the Amino Acid Sequence of Two Proteins", *J. Mol. Biol.*, 48(3):444-453 (1970).

Ono et al., "DNA Triplex Formation of Oligonucleotide Analogs Consisting of Linker Groups and Octamer Segments That Have Opposite Sugar-Phosphate Backbone Polarities", *Biochemistry*, 30: 9914 (1991).
Pearson, "Using the FASTA Program to Search Protein and DNA Sequence Databases", *Methods Mol Biol*, 25:365-389 (1994).
Perrault et al., "Mixed Deoxyribo- and Ribo-Oligonucleotides with Catalytic Activity", *Nature*, 344: 565 (1990).
Petersen et al., "Synthesis and Oligomerization of $N^\delta$-Boc-$N^\alpha$-(Thymin-1-ylacetyl)Ornithine", *Bioorganic & Medicinal Chemistry Letters*, 6(7): 793-796 (1996).
Pieken et al., "Kinetic Characterization of Ribonuclease-Resistant 2'-Modified Hammerhead Ribozymes", *Science*, 253:314 (1991).
Richardson et al., "Tethered Oligonucleotide Probes. A Strategy for the recognition of Structured RNA", *J. Am. Chem. Soc.*, 113(13): 5109 (1991).
SantaLucia et al., "Improved Nearest-Neighbor Parameters for Predicting DNA Duplex Stability", *Biochemistry*, 35: 3555-3562 (1996).
Scaringe et al., "Chemical Synthesis of Biologically Active Oligoribonucleotides Using β-cyanoethyl Protected Ribonucleoside Phosphoramidites", *Nucleic Acids Res.*, 18:5433 (1990).
Seela et al., "Oligodeoxyribonucleotides Containing 1, 3-Propanedioal as Nucleoside Substitute", *Nucleic Acids Res.*, 15:3113 (1987).
Sugimoto et al., "Thermodynamic Parameters to Predict Stability of RNA/DNA Hybrid Duplexes", *Biochemistry*, 34: 11211-11216 (1995).
Usman et al., "Chemical Modification of Hammerhead Ribozymes: Activity and Nuclease Resistance", *Nucleic Acids Symp. Ser.*, 31:163-164 (1994).
Usman et al., "Exploiting the Chemical Synthesis of RNA", *TIBS*, 17: 334-339 (1992).
Usman et al., "The Automated Chemical Synthesis of Long Oligoribuncleotides using 2'-O-Silylated Ribonucleoside 3'-O-Phosphoramidites on a Controlled-Pore Glass Support: Synthesis of a 43-Nucleotide Sequence Similar to the 3'-Half Molecule of an *Escherichia coli* Formylmethionine tRNA", *J. Am. Chem. Soc.*, 109:7845 (1987).
Wincott et al., "A Practical Method for the Production of RNA and Ribozymes", *Methods Mol. Bio.*, 74:59 (1997).
Wincott et al., "Synthesis, Deprotection, Analysis and Purification of RNA and Ribosomes", *Nucleic Acids Res.*, 23 (14):2677-2684 (1995).
Wu et al., "The Ligation Amplification Reaction (LAR)—Amplification of Specific DNA Sequences Using Sequential Rounds of Template-Dependent Ligation",*Genomics*, 4:560 (1989).
Malkov et al. "Multiplexed Measurements of Gene Signatures in Different Analytes Using the Nanostring nCounter™ Assay System." *BMC Res. Notes*. 2.1(2009):80.
Pöhlmann. "Elektrochemische Detektion von RNA mittels Nukleinsäurehybridisierung." *Bayreuth*. (2009):1-203. (German Original and English Summary).
Alfano et al., "Optical Sensing, Imaging, and Manipulation for Biological and biomedical applications" SPIE—The International Society for Optical Engineering, Jul. 2000, vol. 4082, Taiwan.
Ferguson et al., "High-Density Fiber-Optic DNA Random Microsphere Array" *Analytical Chemistry* 72 (22), 5618-5624 (2000).
Steemers et al., "Screening unlabeled DNA targets with randomly ordered fiber-optic gene arrays." *Nature Biotechnology*. 18, 91-94 (2000).
Werner et al., "Current status of DNA sequencing by single molecule detection" Proc. SPIE 3602, Advances in Fluorescence Sensing Technology IV, 355, (1999).

\* cited by examiner

SEQUENCE LISTING

```
<160> NUMBER OF SEQ ID NOS: 35

<210> SEQ ID NO 1
<211> LENGTH: 22
<212> TYPE: RNA
<213> ORGANISM: Homo sapiens

<400> SEQUENCE: 1
ugagguagua gguuguauag uu                                              22

<210> SEQ ID NO 2
<211> LENGTH: 22
<212> TYPE: RNA
<213> ORGANISM: Homo sapiens

<400> SEQUENCE: 2
ugagguagua gguugugugg uu                                              22

<210> SEQ ID NO 3
<211> LENGTH: 22
<212> TYPE: RNA
<213> ORGANISM: Homo sapiens

<400> SEQUENCE: 3
ugagguagua gguuguaugg uu                                              22

<210> SEQ ID NO 4
<211> LENGTH: 21
<212> TYPE: RNA
<213> ORGANISM: Homo sapiens

<400> SEQUENCE: 4
agagguagua gguugcauag u                                               21

<210> SEQ ID NO 5
<211> LENGTH: 21
<212> TYPE: RNA
<213> ORGANISM: Homo sapiens

<400> SEQUENCE: 5
```
ugagguagga gguuguauag u         21

<210> SEQ ID NO 6
<211> LENGTH: 22
<212> TYPE: RNA
<213> ORGANISM: Homo sapiens

<400> SEQUENCE: 6
ugagguagua gauuguauag uu        22

<210> SEQ ID NO 7
<211> LENGTH: 21
<212> TYPE: RNA
<213> ORGANISM: Homo sapiens

<400> SEQUENCE: 7
ugagguagua guuuguacag u         21

<210> SEQ ID NO 8
<211> LENGTH: 21
<212> TYPE: RNA
<213> ORGANISM: Homo sapiens

<400> SEQUENCE: 8
ugagguagua guuugugcug u         21

<210> SEQ ID NO 9
<211> LENGTH: 21
<212> TYPE: RNA
<213> ORGANISM: Homo sapiens

<400> SEQUENCE: 9
uggaauguaa agaaguaugu a         21

<210> SEQ ID NO 10
<211> LENGTH: 22
<212> TYPE: RNA
<213> ORGANISM: Homo sapiens

<400> SEQUENCE: 10
aacccguaga uccgaacuug ug        22

<210> SEQ ID NO 11
<211> LENGTH: 45
<212> TYPE: DNA
<213> ORGANISM: Homo sapiens

<400> SEQUENCE: 11
gggcttgaca tcggcgacac aaaatgcttc taactcgctg tgaat         45

<210> SEQ ID NO 12
<211> LENGTH: 48
<212> TYPE: DNA
<213> ORGANISM: Homo sapiens

<400> SEQUENCE: 12
gggatatatt cctttttttt gcaattaaac tgcccaggcg atctgttg      48

<210> SEQ ID NO 13
<211> LENGTH: 42
<212> TYPE: DNA
<213> ORGANISM: Homo sapiens

<400> SEQUENCE: 13
gctgcgtagt ttatctgcat cactcgtact gaaatgctca ca         42

<210> SEQ ID NO 14
<211> LENGTH: 47
<212> TYPE: DNA
<213> ORGANISM: Homo sapiens

<400> SEQUENCE: 14
ggagtagttt gtccttctgg aatttcttcc tttgattttg ccatttt    47

<210> SEQ ID NO 15
<211> LENGTH: 46
<212> TYPE: DNA
<213> ORGANISM: Homo sapiens

<400> SEQUENCE: 15
gtcgaagtcc ttcgagtgca tgagctgtct ttcacatgat acatcg     46

<210> SEQ ID NO 16
<211> LENGTH: 44
<212> TYPE: DNA
<213> ORGANISM: Homo sapiens

<400> SEQUENCE: 16
ggtggggctt gtcgactgat agtaactgtg gttcgagtta tgcg       44

<210> SEQ ID NO 17
<211> LENGTH: 44
<212> TYPE: DNA
<213> ORGANISM: Homo sapiens

<400> SEQUENCE: 17
gacggtccta gaagtcaaaa agctgcttga tcgaaaaaaa gcag       44

<210> SEQ ID NO 18
<211> LENGTH: 48
<212> TYPE: DNA
<213> ORGANISM: Homo sapiens

<400> SEQUENCE: 18
ggttttaata gcgcgagaac aagtgagacg tgtatagttg ccatgctg   48

<210> SEQ ID NO 19
<211> LENGTH: 44
<212> TYPE: DNA
<213> ORGANISM: Homo sapiens

<400> SEQUENCE: 19
gccgtgaccc aactctattc ccattgcctc caaaccagcc cttg       44

<210> SEQ ID NO 20
<211> LENGTH: 52
<212> TYPE: DNA
<213> ORGANISM: Homo sapiens

<400> SEQUENCE: 20
gaaaaataaa aagtaaattg ggcaatacca ccaaaatcgt tctttatggg gt   52

<210> SEQ ID NO 21
<211> LENGTH: 28
<212> TYPE: DNA
<213> ORGANISM: Homo sapiens

```
<400> SEQUENCE: 21
tgtcaagccc aactatacaa cctactac                                              28

<210> SEQ ID NO 22
<211> LENGTH: 29
<212> TYPE: DNA
<213> ORGANISM: Homo sapiens

<400> SEQUENCE: 22
aaggaatata tcccaaccac acaacctac                                             29

<210> SEQ ID NO 23
<211> LENGTH: 26
<212> TYPE: DNA
<213> ORGANISM: Homo sapiens

<400> SEQUENCE: 23
actacgcagc aaccatacaa cctact                                                26

<210> SEQ ID NO 24
<211> LENGTH: 29
<212> TYPE: DNA
<213> ORGANISM: Homo sapiens

<400> SEQUENCE: 24
gacaaactac tccaactatg caacctact                                             29

<210> SEQ ID NO 25
<211> LENGTH: 26
<212> TYPE: DNA
<213> ORGANISM: Homo sapiens

<400> SEQUENCE: 25
aggacttcga caactataca acctcc                                                26

<210> SEQ ID NO 26
<211> LENGTH: 28
<212> TYPE: DNA
<213> ORGANISM: Homo sapiens

<400> SEQUENCE: 26
agccccacca actatacaat ctactacc                                              28

<210> SEQ ID NO 27
<211> LENGTH: 30
<212> TYPE: DNA
<213> ORGANISM: Homo sapiens

<400> SEQUENCE: 27
ctaggaccgt caactgtaca aactactacc                                            30

<210> SEQ ID NO 28
<211> LENGTH: 31
<212> TYPE: DNA
<213> ORGANISM: Homo sapiens

<400> SEQUENCE: 28
cgctattaaa accaacagca caaactacta c                                          31

<210> SEQ ID NO 29
<211> LENGTH: 28
<212> TYPE: DNA
```

```
<213> ORGANISM: Homo sapiens

<400> SEQUENCE: 29
ggtcacggca tacatacttc tttacatt                                          28

<210> SEQ ID NO 30
<211> LENGTH: 32
<212> TYPE: DNA
<213> ORGANISM: Homo sapiens

<400> SEQUENCE: 30 tttactttt atttttccac aagttcggat ct                                      32

<210> SEQ ID NO 31
<211> LENGTH: 18
<212> TYPE: RNA
<213> ORGANISM: Homo sapiens

<400> SEQUENCE: 31
guaguagguu guauaguu                                                     18

<210> SEQ ID NO 32
<211> LENGTH: 15
<212> TYPE: RNA
<213> ORGANISM: Homo sapiens

<400> SEQUENCE: 32
guagguugug ugguu                                                        15

<210> SEQ ID NO 33
<211> LENGTH: 16
<212> TYPE: RNA
<213> ORGANISM: Homo sapiens

<400> SEQUENCE: 33
aguagguugu augguu                                                       16

<210> SEQ ID NO 34
<211> LENGTH: 16
<212> TYPE: RNA
<213> ORGANISM: Homo sapiens

<400> SEQUENCE: 34
aguagguugc auaguu                                                       16

<210> SEQ ID NO 35
<211> LENGTH: 15
<212> TYPE: RNA
<213> ORGANISM: Homo sapiens

<400> SEQUENCE: 35
ggagguugua uaguu                                                        15
```

COMPOSITIONS AND METHODS FOR THE DETECTION OF SMALL RNAS

RELATED APPLICATIONS

This application claims priority from U.S. Provisional Patent Application 61/303,517 filed on Feb. 11, 2010 and incorporated, herein, in its entirety.

INCORPORATION OF SEQUENCE LISTING

The contents of the text file named "40448-508001US_ST25.txt," which was created on Apr. 20, 2011 and is 5.38 KB in size, are hereby incorporated by reference in their entirety.

FIELD OF THE INVENTION

This invention relates generally to the field of molecular biology, and specifically, to the fields of detection, identification, and quantification of target nucleic acid molecules in mixtures.

BACKGROUND OF THE INVENTION

Although all cells in the human body contain the same genetic material, the same genes are not active in all of those cells. Alterations in gene expression patterns can have profound effects on biological functions. These variations in gene expression are at the core of altered physiologic and pathologic processes. Therefore, identifying and quantifying the expression of genes in normal cells compared to diseased cells can aid the discovery of new drug and diagnostic targets.

Nucleic acids can be detected and quantified based on their specific polynucleotide sequences. The basic principle underlying existing methods of detection and quantification is the hybridization of a labeled complementary probe sequence to a target sequence of interest in a sample. The formation of a duplex indicates the presence of the target sequence in the sample.

This technique, called molecular hybridization, has been a useful tool for identifying and analyzing specific nucleic acid sequences in complex mixtures. This technique has been used in diagnostics, for example, to detect nucleic acid sequences of various microbes in biological samples. In addition, hybridization techniques have been used to map genetic differences or polymorphisms between individuals. Furthermore, these techniques have been used to monitor changes in gene expression in different populations of cells or in cells treated with different agents.

The identification of small RNA molecules, microRNA (miRNA) molecules, with hybridization techniques presents several unique challenges. Hybridization of a detection probe to a short length RNA molecule of a typical miRNA target occurs at low melting temperatures and prevents concurrent binding by multiple detection moieties. Low melting temperature hybridizations are unfavorable for specific binding of multiple probes to target miRNA sequences that may differ by only a single nucleic acid. Furthermore, miRNA sequences demonstrate great diversity despite having constant or conserved lengths, which generates a large variety of hybridization melting temperatures.

Thus, there exists a need for accurate and sensitive detection, identification and quantification of target nucleic acid molecules in complex mixtures. Particularly, there exists a need for the specific detection of small RNA molecules, such as miRNA molecules, in complex mixtures or multiplex reactions.

SUMMARY OF THE INVENTION

Compositions and methods of the invention provide a solution for the long felt need for the specific detection of small RNA molecules, such as miRNA molecules, in complex mixtures or multiplex reactions. This can be achieved by ligation of any small RNA molecule to a unique, sequence-specific tag molecule at a single temperature by normalizing the melting temperature of hybridization between the target small RNA and a bridge molecule which directs the specific attachment of a unique tag. The ligated tags subsequently normalize the melting temperatures of the mixed population of tagged small RNAs, allowing them to be subjected to a multiplexed hybridization assay in which it is possible to distinguish small RNAs in a sequence-specific manner at the same temperature.

Specifically, the invention provides a composition including: (a) a tag, wherein the tag includes a first DNA sequence and a reporter attachment region to which are attached one or more reporter molecules that produce a signal and wherein the first DNA sequence includes an alien DNA sequence; and (b) a bridge, wherein the bridge includes a second DNA sequence that is complementary to a RNA molecule and a third DNA sequence that is complementary to the first DNA sequence of the tag.

In one aspect of this composition the second DNA sequence is complementary to a RNA molecule or a portion thereof. A portion of the RNA molecule is less than the entire length of the RNA molecule. In certain aspects the portion is 10%, 20%, 30%, 40%, 50%, 60%, 70%, 80%, 90%, 99%, or any percentage point in between of the entire length of the RNA molecule. Moreover, the portion is either continuous or discontinuous.

In another aspect of the composition, the first DNA sequence of the tag includes alien DNA, wherein the alien DNA does not cross-hybridize with any other DNA or RNA molecule in the composition other than the third DNA sequence of the bridge. Alternatively, or in addition, the alien DNA cross-hybridizes with less than 15% of DNA and RNA molecules in the composition other than the third DNA sequence of the bridge. Specifically, the alien DNA sequence cross-hybridizes with no greater than 15%, 10%, 5%, 2%, 1% or any percentage point in between, of DNA and RNA molecules in the composition other than the third DNA sequence of the bridge. In certain aspects of the composition, the tag contains a first DNA sequence composed of alien DNA, which has no greater than 85% identity across 35 bases with a maximum continuous homology of 15 bases or less to any known DNA or RNA sequence in the composition. Alternatively, the alien DNA has no greater than 85% identity across 35 bases with a maximum continuous homology of 15 bases or less to any known genomic DNA or RNA sequence. Moreover, the alien DNA has no greater than 85% identity across 35 bases with a maximum continuous homology of 15 bases or less to any known DNA or RNA sequence from or transcribed by a genome from which the target RNA molecule is transcribed. Target RNA molecules are from or transcribed by the genomes of any species, including, but not limited to, animals, plants, bacteria, fungi and viruses. Preferred species are mammals, including primates, preferably humans and rodents including rabbit, rat and mice.

In certain aspects of the tag, the first DNA sequence and the reporter attachment region are tangential or overlapping. The first DNA sequence and the reporter attachment region may overlap by a number of DNA nucleotides ranging from 1-5, 5-10, 10-15, 15-20, 20-25, 25-30, 30-35, 35-40, 40-45, 45-50, 50-55, 55-60, 60-65, 65-70, 75-80, 80-85, 85-90, 90-95, 95-100, or any number of nucleotides in between. Moreover, the first DNA sequence and the reporter attachment region may overlap by a percentage of the total number of nucleotides present in the first DNA sequence ranging from 1-5%, 5-10%, 10-15%, 15-20%, 20-25%, 25-30%, 30-35%, 35-40%, 40-45%, 45-50%, 50-55%, 55-60%, 60-65%, 65-70%, 75-80%, 80-85%, 85-90%, 90-95%, 95-100%, or any percentage of nucleotides of the first DNA sequence in between. In a particular aspect, the reporter attachment region may be entirely contained within the first DNA sequence.

In one embodiment of the composition, the second and third DNA sequences of the bridge are contiguous. Alternatively, the second and third DNA sequences are connected by a linker molecule containing at least two deoxyribonucleotides. In certain aspects of the composition, the linker molecule contains between 2-100 deoxyribonucleotides, and specifically, between 2-10 deoxyribonucleotides, 10-20 deoxyribonucleotides, 20-30 deoxyribonucleotides, 30-40 deoxyribonucleotides, 40-50 deoxyribonucleotides, 50-60 deoxyribonucleotides, 60-70 deoxyribonucleotides, 70-80 deoxyribonucleotides, 80-90 deoxyribonucleotides, 90-100 deoxyribonucleotides, or any number of deoxyribonucleotides in between. The linker molecule may contain deoxyribonucleotide (DNA) sequence obtained or derived from any species, including alien or synthetic sequences.

In certain aspects of the composition, the second DNA sequence of the bridge and the RNA molecule form a DNA/RNA heteroduplex having a melting temperature of between 37-95° C. Alternatively, the second DNA sequence of the bridge and the RNA molecule form a DNA/RNA heteroduplex having a melting temperature of between 44-53° C. In other aspects, the third DNA sequence of the bridge and the first sequence of the tag form a DNA/DNA duplex having a melting temperature of between 37-95° C. Alternatively, the third DNA sequence of the bridge and the first sequence of the tag form a DNA/DNA duplex having a melting temperature of between 44-53° C.

In a preferred embodiment of the composition, the second and third DNA sequences of the bridge form nucleic acid duplexes having substantially the same melting temperature. In certain aspects, the second and third DNA sequences of the bridge form nucleic acid duplexes having melting temperatures within 1° C., 2° C., 5° C., 10° C., 15° C., 20° C., or any degree in between of one another. Preferably, the second and third DNA sequences of the bridge form nucleic acid duplexes having melting temperatures within 1° C., 2° C., or 5° C. of one another.

In another embodiment of the composition, the third DNA sequence includes an alien DNA sequence. In one aspect of this embodiment, the third DNA sequence includes a portion of an alien DNA sequence.

In another embodiment of the composition, the RNA comprises a non-coding RNA. Exemplary non-coding RNA include, but are not limited to, a transfer RNA (tRNA), a small nucleolar RNA (snoRNA), a microRNA (miRNA), a short interfering RNA (siRNA), a short hairpin RNA (shRNA), a repeat associated small interfering RNA (rasiRNA), and a piwi-interacting RNA (piRNA). In a preferred aspect, the non-coding RNA is a miRNA. Alternatively or in addition, the RNA molecule includes between 10-300 ribonucleotides.

In certain embodiments of the composition, the RNA molecule and/or the tag contain sequences that specifically hybridize to the bridge with complete complementarity. Alternatively, or in addition, the RNA molecule and/or the tag contain sequences that specifically hybridize to the bridge with partial complementarity. In certain aspects, partial complementarity is defined as less than complete or less than 100% complementarity. Alternatively, partial complementarity is defined as binding with less than 100%, 90%, 80%, 70%, 60%, 50%, 40%, 30%, 20%, 10%, or any percentage value in between.

The invention further provides a kit containing: (a) a composition including: (1) a tag, wherein the tag includes a first DNA sequence and a reporter attachment region to which are attached one or more reporter molecules that produce a signal; and (2) a bridge, wherein the bridge includes a second DNA sequence that is complementary to a RNA molecule and a third DNA sequence that is complementary to the first DNA sequence of the tag; and (b) a substance selected from the group consisting of a volume excluder and a nuclease. Optionally, the kit further includes a ligase.

In one embodiment of the kit, the selected substance is a volume excluder. A nonlimiting example of a preferred volume excluder is polyethylene glycol (PEG).

In another embodiment of the kit, the selected substance is a nuclease. The nuclease is preferably a DNA-specific exonuclease. A nonlimiting example of a DNA-specific exonuclease is a lambda exonuclease.

In certain embodiments of the kit, the second and third DNA sequences of the bridge are contiguous. Alternatively, the second and third DNA sequences are connected by a linker molecule. In certain aspects of the kit, the linker molecule contains between 2-100 deoxyribonucleotides, and specifically, between 2-10 deoxyribonucleotides, 10-20 deoxyribonucleotides, 20-30 deoxyribonucleotides, 30-40 deoxyribonucleotides, 40-50 deoxyribonucleotides, 50-60 deoxyribonucleotides, 60-70 deoxyribonucleotides, 70-80 deoxyribonucleotides, 80-90 deoxyribonucleotides, 90-100 deoxyribonucleotides, or any number of deoxyribonucleotides in between. The linker molecule may contain deoxyribonucleotide (DNA) sequence obtained or derived from any species, including alien sequences.

In other embodiments of the kit, the second DNA sequence of the bridge and the RNA molecule form a DNA/RNA heteroduplex having a melting temperature of between 37-95° C. Alternatively, the second DNA sequence of the bridge and the RNA molecule form a DNA/RNA heteroduplex having a melting temperature of between 44-53° C. In a further embodiment, the third DNA sequence of the bridge and the first sequence of the tag form a DNA/DNA duplex having a melting temperature of between 37-95° C. Alternatively, the third DNA sequence of the bridge and the first sequence of the tag form a DNA/DNA duplex having a melting temperature of between 44-53° C.

In a preferred embodiment, the second and third DNA sequences of the bridge form nucleic acid duplexes having substantially the same melting temperature. In certain aspects, the second and third DNA sequences of the bridge form nucleic acid duplexes having melting temperatures within 1° C., 2° C., 5° C., 10° C., 15° C., 20° C., or any degree in between of one another. Preferably, the second and third DNA sequences of the bridge form nucleic acid duplexes having melting temperatures within 1° C., 2° C., or 5° C. of one another.

In another preferred embodiment, the third DNA sequence includes an alien DNA sequence.

In certain embodiments of the kit, the RNA molecule and/or the tag contain sequences that specifically hybridize to the bridge with complete complementarity. Alternatively, or in addition, the RNA molecule and/or the tag contain sequences that specifically hybridize to the bridge with partial complementarity. In certain aspects, partial complementarity is defined as less than complete or less than 100% complementarity. Alternatively, partial complementarity is defined as binding with less than 100%, 90%, 80%, 70%, 60%, 50%, 40%, 30%, 20%, or 10% complementarity or any percentage value in between.

The invention further provides a method of detecting a RNA molecule including: (a) providing a sample containing at least one RNA molecule; (b) providing a tag, wherein the tag includes a first DNA sequence and a reporter attachment region to which are attached one or more reporter molecules that produce a signal; (c) providing a bridge, wherein the bridge includes a second DNA sequence that is complementary to the RNA molecule and a third DNA sequence that is complementary to the first DNA sequence of the tag; and (d) providing a buffer; (e) specifically annealing the RNA molecule, bridge, and tag at between 37-95° C.; (f) holding the annealed reaction at between 37-95° C.; (g) providing a ligase buffer; (h) providing a ligase directly to annealed reaction at between 37-95° C.; (i) ligating the RNA molecule to the tag at one or more temperatures between 37-95° C.; and (j) detecting the signal.

In certain embodiments, this method of detecting a RNA molecule further includes the step of denaturing the RNA molecule, bridge, and tag prior to specifically annealing the RNA molecule, bridge, and tag at between 37-95° C.

In another embodiment of this method, steps (e), (f), (h), and (i) are performed at between 43-52° C.

In other embodiments, this method of detecting a RNA molecule further includes providing a volume excluder after holding the annealed reaction at between 37-95° C. A nonlimiting example of a volume excluder is polyethylene glycol (PEG).

In certain embodiments, the method further includes providing a nuclease to the ligation reaction after ligating the RNA molecule to the tag at between 37-95° C. In one aspect, the nuclease is a DNA-specific exonuclease. A nonlimiting example of the DNA-specific exonuclease is a lambda exonuclease.

In a preferred embodiment of this method of detecting a RNA molecule, the second and third DNA sequences of the bridge are contiguous. Alternatively, the second and third DNA sequences are connected by a linker molecule. In certain aspects of this method, the linker molecule contains between 2-100 deoxyribonucleotides, and specifically, between 2-10 deoxyribonucleotides, 10-20 deoxyribonucleotides, 20-30 deoxyribonucleotides, 30-40 deoxyribonucleotides, 40-50 deoxyribonucleotides, 50-60 deoxyribonucleotides, 60-70 deoxyribonucleotides, 70-80 deoxyribonucleotides, 80-90 deoxyribonucleotides, 90-100 deoxyribonucleotides, or any number of deoxyribonucleotides in between. The linker molecule may contain deoxyribonucleotide (DNA) sequence obtained or derived from any species, including alien sequences.

In another embodiment of this method of detecting a RNA molecule, the RNA comprises a non-coding RNA. Exemplary non-coding RNA include, but are not limited to, a transfer RNA (tRNA), a small nucleolar RNA (snoRNA), a microRNA (miRNA), a short interfering RNA (siRNA), a short hairpin RNA (shRNA), a repeat associated small interfering RNA (rasiRNA), and a piwi-interacting RNA (piRNA). In a preferred aspect of this method, the non-coding RNA is a miRNA.

In certain embodiments of this method of detecting a RNA molecule, the second DNA sequence of the bridge and the RNA molecule form a DNA/RNA heteroduplex having a melting temperature of between 37-95° C. Alternatively, the second DNA sequence of the bridge and the RNA molecule form a DNA/RNA heteroduplex having a melting temperature of between 44-53° C. In other embodiments, the third DNA sequence of the bridge and the first sequence of the tag form a DNA/DNA duplex having a melting temperature of between 37-95° C. Alternatively, the third DNA sequence of the bridge and the first sequence of the tag form a DNA/DNA duplex having a melting temperature of between 44-53° C.

In a preferred embodiment of this method of detecting a RNA molecule, the second and third DNA sequences of the bridge form nucleic acid duplexes having substantially the same melting temperature. In certain aspects, the second and third DNA sequences of the bridge form nucleic acid duplexes having melting temperatures within 1° C., 2° C., 5° C., 10° C., 15° C., 20° C., or any degree in between of one another. Preferably, the second and third DNA sequences of the bridge form nucleic acid duplexes having melting temperatures within 1° C., 2° C., or 5° C. of one another.

In one embodiment of this method of detecting a RNA molecule, the third DNA sequence comprises an alien DNA sequence.

In certain aspects of this method of detecting a RNA molecule, the RNA molecule and/or the tag contain sequences that specifically hybridize to the bridge with complete complementarity. Alternatively, or in addition, the RNA molecule and/or the tag contain sequences that specifically hybridize to the bridge with partial complementarity. In certain aspects, partial complementarity is defined as less than complete or less than 100% complementarity. Alternatively, partial complementarity is defined as binding with less than 100%, 90%, 80%, 70%, 60%, 50%, 40%, 30%, 20%, or 10% complementarity, or any percentage value in between.

The invention further provides a method of multiplex detection of a plurality of RNA molecules including: (a) providing a sample containing a plurality of RNA molecules; (b) providing a plurality of tags, wherein each tag includes a first DNA sequence and at least one reporter attachment region to which are attached one or more reporter molecules that produce a signal; (c) providing a plurality of bridges, wherein each bridge includes a second DNA sequence that is complementary to one RNA molecule and a third DNA sequence that is complementary to the first DNA sequence of one tag, wherein each bridge specifically anneals to one species of RNA molecule and one species of tag, wherein the one species of tag produces a signal that differentially labels one species of RNA molecule compared to other species of RNA molecules when it is joined to the tag; (d) providing a buffer; (e) specifically annealing the RNA molecules, bridges, and tags at between 37-95° C.; (f) holding the annealed reaction at between 37-95° C.; (g) providing a ligase buffer; (h) providing a ligase directly to annealed reaction at between 37-95° C.; (i) ligating the RNA molecules, bridges, and tags at one or more temperatures between 37-95° C.; and (j) detecting one or more signals.

In one embodiment, this method of multiplex detection of a plurality of RNA molecules further includes the step of denaturing the RNA molecules, bridges, and tags prior to specifically annealing the RNA molecules, bridges, and tags at between 37-95° C.

In another embodiment of this method of multiplex detection of a plurality of RNA molecules, steps (e), (f), (h), and (i) are performed at between 43-52° C.

In certain embodiments, this method of multiplex detection of a plurality of RNA molecules further includes providing a volume excluder after holding the annealed reaction at between 37-95° C. A nonlimiting example of the volume excluder is polyethylene glycol (PEG). Alternatively, or in addition, the method further includes providing a nuclease to the ligation reaction after ligating the RNA molecule to the tag at between 37-95° C. In one aspect, the nuclease is a DNA-specific exonuclease. A nonlimiting example of the DNA-specific exonuclease is a lambda exonuclease.

In a preferred embodiment of this method of multiplex detection of a plurality of RNA molecules, the second and third DNA sequences of the bridges are contiguous. Alternatively, the second and third DNA sequences are connected by a linker molecule. In certain aspects of this method, the linker molecule contains between 2-100 deoxyribonucleotides, and specifically, between 2-10 deoxyribonucleotides, 10-20 deoxyribonucleotides, 20-30 deoxyribonucleotides, 30-40 deoxyribonucleotides, 40-50 deoxyribonucleotides, 50-60 deoxyribonucleotides, 60-70 deoxyribonucleotides, 70-80 deoxyribonucleotides, 80-90 deoxyribonucleotides, 90-100 deoxyribonucleotides, or any number of deoxyribonucleotides in between. The linker molecule may contain deoxyribonucleotide (DNA) sequence obtained or derived from any species, including alien sequences.

In another preferred embodiment, the third DNA sequence includes an alien DNA sequence.

In another embodiment of this method of multiplex detection of a plurality of RNA molecules, the RNA molecules comprise a non-coding RNA. Nonlimiting examples of the non-coding RNA include, but are not limited to, a transfer RNA (tRNA), a small nucleolar RNA (snoRNA), a microRNA (miRNA), a short interfering RNA (siRNA), a short hairpin RNA (shRNA), a repeat associated small interfering RNA (rasiRNA), or a piwi-interacting RNA (piRNA). Preferably, the non-coding RNA is a miRNA.

In certain embodiments of this method of multiplex detection of a plurality of RNA molecules, the second DNA sequence of the bridges and the RNA molecules form a DNA/RNA heteroduplex having a melting temperature of between 37-95° C. Alternatively, the second DNA sequence of the bridges and the RNA molecules form a DNA/RNA heteroduplex having a melting temperature of between 44-53° C. In other embodiments, the third DNA sequence of the bridges and the first sequence of the tags form a DNA/DNA duplex having a melting temperature of between 37-95° C. Alternatively, the third DNA sequence of the bridges and the first sequence of the tags form a DNA/DNA duplex having a melting temperature of between 44-53° C.

In a preferred embodiment of this method of multiplex detection of a plurality of RNA molecules, the second and third DNA sequences of the bridge form nucleic acid duplexes having substantially the same melting temperature. In certain aspects, the second and third DNA sequences of the bridge form nucleic acid duplexes having melting temperatures within 1° C., 2° C., 5° C., 10° C., 15° C., 20° C., or any degree in between of one another. Preferably, the second and third DNA sequences of the bridge form nucleic acid duplexes having melting temperatures within 1° C., 2° C., or 5° C. of one another.

In one embodiment of this method of multiplex detection of a plurality of RNA molecules, the RNA molecules and/or the tags contain sequences that specifically hybridize to the bridge with complete complementarity. Alternatively, or in addition, the RNA molecules and/or the tags contain sequences that specifically hybridize to the bridge with partial complementarity. In certain aspects, partial complementarity is defined as less than complete or less than 100% complementarity. Alternatively, partial complementarity is defined as binding with less than 100%, 90%, 80%, 70%, 60%, 50%, 40%, 30%, 20%, 10%, or any percentage value in between.

The invention also provides a method of making a nucleic acid bridge molecule, including: (a) selecting a RNA molecule; (b) selecting a segment of the RNA molecule that forms a DNA/RNA heteroduplex with a DNA molecule that specifically hybridizes to the segment of the RNA molecule having a melting temperature of between 37-95° C.; (c) generating a first DNA bridge molecule that specifically hybridizes to the segment of the RNA molecule having a melting temperature of between 37-95° C.; (d) selecting a tag, wherein the tag includes a DNA sequence that is an alien sequence; (e) selecting a segment of the tag that forms a DNA/DNA duplex with a DNA molecule that specifically hybridizes to the segment of the tag having a melting temperature of between 37-95° C.; (f) generating a second DNA bridge molecule that specifically hybridizes to the segment of the tag having a melting temperature of between 37-95° C.; and (g) uniting the first DNA bridge molecule with the second DNA bridge molecule, thereby forming the nucleic acid DNA bridge molecule that specifically hybridizes to the segment of the target RNA molecule having a melting temperature of between 37-95° C. and the segment of the tag having a melting temperature of between 37-95° C.

In certain embodiments of this method of making a nucleic acid bridge molecule, the uniting step includes ligating the first DNA bridge molecule to the second DNA bridge molecule. Alternatively, the uniting step includes synthesizing a nucleic acid DNA bridge molecule containing the sequence of the first DNA bridge molecule and the sequence of the second DNA bridge molecule.

In a preferred embodiment of this method of making a nucleic acid bridge molecule, the first DNA bridge molecule and the second DNA bridge molecule have substantially the same melting temperature. In certain aspects, the second and third DNA sequences of the bridge form nucleic acid duplexes having melting temperatures within 1° C., 2° C., 5° C., 10° C., 15° C., 20° C., or any degree in between of one another. Preferably, the second and third DNA sequences of the bridge form nucleic acid duplexes having melting temperatures within 1° C., 2° C., or 5° C. of one another.

In another preferred embodiment of this method of making a nucleic acid bridge molecule, the second DNA bridge molecule is selected from the 5' end of the first DNA sequence of the tag. Specifically, the second DNA molecule is selected from a portion of the first DNA sequence of the tag that includes between 2-5 nucleotides, 2-10 nucleotides, 2-20 nucleotides, 2-30 nucleotides, 2-40 nucleotides, 2-50 nucleotides, 2-60 nucleotides, 2-70 nucleotides, 2-80 nucleotides, 2-90 nucleotides, 2-100 nucleotides or any range in between of nucleotides from the 5' end of the first DNA sequence of the tag. Preferably, the second DNA molecule is selected from a portion of the first DNA sequence of the tag that includes between 2-10 nucleotides or between 2-20 nucleotides from the 5' end of the first DNA sequence of the tag.

In particular embodiments of this method of making a nucleic acid bridge molecule, the DNA/RNA heteroduplex has a melting temperature of between 43-52° C. Alternatively, or in addition, the DNA/DNA duplex has a melting temperature of between 43-52° C.

In a preferred embodiment of this method of making a nucleic acid bridge molecule, the first DNA bridge molecule and the second DNA bridge molecule are contiguous. Alternatively, the second and third DNA sequences are connected by a linker molecule. In certain aspects of this method, the linker molecule contains between 2-100 deoxyribonucleotides, and specifically, between 2-10 deoxyribonucleotides, 10-20 deoxyribonucleotides, 20-30 deoxyribonucleotides, 30-40 deoxyribonucleotides, 40-50 deoxyribonucleotides, 50-60 deoxyribonucleotides, 60-70 deoxyribonucleotides, 70-80 deoxyribonucleotides, 80-90 deoxyribonucleotides, 90-100 deoxyribonucleotides, or any number of deoxyribonucleotides in between. The linker molecule may contain deoxyribonucleotide (DNA) sequence obtained or derived from any species, including alien sequences.

In other embodiments of this method of making a nucleic acid bridge molecule, the RNA molecule is a miRNA. Alternatively, the RNA molecule includes a non-coding RNA. Preferably, the non-coding RNA is a miRNA.

Particularly in those embodiments of this method of making a nucleic acid bridge molecule wherein the RNA molecule is an miRNA, but with respect to all embodiments presented herein, the first DNA bridge molecule hybridizes to the RNA molecule with complete complementarity. Alternatively, the first DNA bridge molecule hybridizes to the RNA molecule with partial complementarity. With respect to all embodiments presented herein, the second DNA bridge molecule hybridizes to the tag with complete complementarity. Alternatively, the second DNA bridge molecule hybridizes to the tag with partial complementarity. In certain aspects, partial complementarity is defined as less than complete or less than 100% complementarity. Alternatively, partial complementarity is defined as binding with less than 100%, 90%, 80%, 70%, 60%, 50%, 40%, 30%, 20%, 10%, or any percentage value in between.

DETAILED DESCRIPTION

The invention provides a sensitive, hybridization-based technology for the multiplexed analysis of mRNA gene expression. In certain embodiments of the invention, the NCOUNTER® Analysis System is used. In mRNA detection experiments using the NCOUNTER® Analysis System, high hybridization reaction temperatures (typically 65° C.) promote the specific target/reporter interaction of a 70-100 base target region. Such assays do not allow for the detection of small nucleic acid species, e.g. miRNAs, due to the low melting temperature ($T_m$) of such short sequences. Thus, the invention solves this problem by providing a novel assay, that may be used in the NCOUNTER® miRNA Expression Assay Kit, which is compatible with the NCOUNTER® Analysis System described herein and allows for specific and sensitive detection of short RNAs, using microRNAs (miRNAs) as a model system. The assay involves attaching a specific DNA tag to each discrete species of small RNA, thereby creating a chimeric RNA-DNA target with a $T_m$ that is high enough to be compatible with the standard hybridization conditions of the NCOUNTER® Analysis System.

The addition of the tag can be done in a multiplexed fashion, such that a single sample can be assayed for hundreds of species of small RNAs simultaneously. A key feature of this invention is the highly specific attachment of each tag under narrowly defined reaction conditions, such that the specificity and efficiency of the tag attachment reaction is retained in a multiplex format where all of the separate interactions are taking place simultaneously and under the same reaction conditions.

Figure 1:
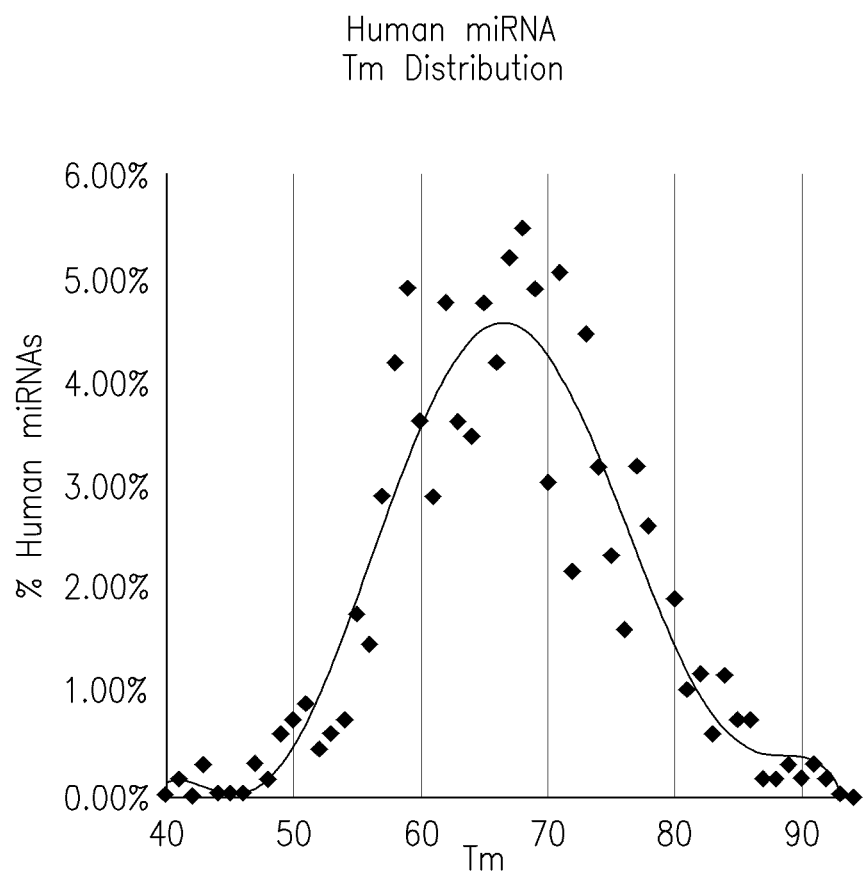
FIG. 1 is a graph depicting human miRNA melting temperature (Tm) distribution as the percentage (%) of human miRNAs versus Tm in degrees Celsius (° C.).

MicroRNAs (miRNAs) are small, endogenous, non-coding, regulatory, single-stranded RNA molecules of about 21-23 nucleotides in length. While miRNAs in general exhibit a great deal of sequence diversity, small groups of miRNAs (miRNA families) exist with >90% sequence identity. Hybridization-based assays for specific detection of nearly identical species are most sensitive when hybridization occurs near the $T_m$ of the target species. Such conditions greatly reduce cross-hybridization between nearly identical sequences by maximizing thermodynamic destabilization between target and mismatched species. The overall sequence diversity of miRNAs and other small RNAs complicates specific multiplexed detection of their expression by hybridization because it means that the optimal hybridization temperature (i.e. target $T_m$) varies from target to target (FIG. 1). A second key feature of the NCOUNTER® miRNA Expression Assay Kit is the target-specific design of each synthetic DNA tag which allows for the normalization of the diverse $T_m$'s of naturally-occurring small RNA sequences; in other words, the individual tags are designed to make the $T_m$'s of the final RNA-DNA chimeras equivalent, regardless of the $T_m$ of the underlying biological RNA sequence. This allows the subsequent hybridization detection assay to be done at a single temperature for all the diverse species, and thus allows for multiplexing of the detection reaction.

MicroRNAs

MicroRNAs (miRNAs) are small, non-coding regulatory RNAs that are hypothesized to act by inhibiting translation of messenger RNA (mRNA) into protein by binding to the 3' untranslated region (UTR) of their target mRNAs. mRNAs inhibit mRNA translation by either causing mRNA degradation or inhibiting translation itself.

mRNAs are single-stranded RNA molecules of about 21-23 nucleotides in length. mRNAs are encoded by endogenous and exogenous genes that are transcribed from genomic DNA; however, miRNAs are typically not translated into polypeptide sequences. As such, miRNAs are considered in the art as "non-coding RNAs." The term "endogenous" gene as used herein is meant to encompass all genes that naturally occur within the genome of an individual. The term "exogenous" gene as used herein is meant to encompass all genes that do not naturally occur within the genome of an individual. For example, a miRNA could be introduced exogenously by a virus.

mRNA molecules of the invention include pri-miRNA, pre-miRNA, and mature miRNAs. Mature miRNAs are initially transcribed from genomic DNA into pri-miRNA. Pri-miRNA contains at least 1 (up to 6 when transcribed from polycistronic units) hairpin loop structures that are each approximately 70 nucleotides in length. There is a potential for a single pri-miRNA to contain multiple miRNAs. Pri-miRNA can also be subject to RNA editing wherein the miRNA processing or specificity is altered. Pri-miRNA is cleaved in the cell nucleus about 11 nucleotides from the base of each hairpin structure (2 helical RNA turns into the stem) to form pre-miRNA. Staggered cuts are introduced into the ends of the hairpin loop arms resulting in a 2 nucleotide overhang on the 3' end and a phosphate on the 5' end to produce a pre-miRNA of approximately 70 nucleotides in length. In the cytoplasm the pre-miRNA is cleaved and results in an imperfect miRNA:miRNA* duplex of approximately 20-25 nucleotide pairs in length that contains the mature miRNA strand and its opposite complementary miRNA* strand. The passenger strand, or complementary miRNA strand*, is normally degraded and present in lower levels in cells in the steady state, although there are instances where both strands of the duplex become functional miRNAs that target different mRNA populations.

The term "miRNA" is equivalent to other terms used to describe nucleic acid molecules that are capable of mediating sequence-specific gene silencing or interference, e.g., short interfering RNA (siRNA), double-stranded RNA (dsRNA), interfering RNA (RNAi), short hairpin RNA (shRNA), short interfering oligonucleotides, short interfering nucleic acid, short interfering chemically-modified siRNA, post-transcriptional gene silencing RNA (ptg-sRNA), and other art-recognized equivalents. As used herein, the term "gene silencing" is meant to describe the downregulation, knock-down, degradation, inhibition, suppression, repression, prevention, or decreased expression of a gene, transcript and/or polypeptide product. Gene silencing and interference also describe the prevention of translation of mRNA transcripts into a polypeptide. Translation is prevented, inhibited, or decreased by degrading mRNA transcripts or blocking mRNA translation.

The bridges of the invention bind specifically to their target miRNAs based on either partial or complete sequence complementarity. Exemplary miRNAs are provided in Table 1, below.

Table 1: Exemplary Human miRNAs

TABLE 1

Exemplary Human miRNAs

| SEQ ID NO: | Sequence | MIRBASE ™ ID |
| --- | --- | --- |
| 1 | UGAGGUAGUAGGUUGUAUAGUU | hsa-let-7a |
| 2 | UGAGGUAGUAGGUUGUGUGGUU | hsa-let-7b |
| 3 | UGAGGUAGUAGGUUGUAUGGUU | hsa-let-7c |
| 4 | AGAGGUAGUAGGUUGCAUAGU | hsa-let-7d |
| 5 | UGAGGUAGGAGGUUGUAUAGU | hsa-let-7e |
| 6 | UGAGGUAGUAGAUUGUAUAGUU | hsa-let-7f |
| 7 | UGAGGUAGUAGUUUGUACAGU | hsa-let-7g |
| 8 | UGAGGUAGUAGUUUGUGCUGU | hsa-let-7i |
| 9 | UGGAAUGUAAAGAAGUAUGUA | hsa-miR-1 |
| 10 | AACCCGUAGAUCCGAACUUGUG | hsa-miR-100 |

All miRNA sequences are publicly available online.

NCOUNTER® Analysis System Protocol Overview and Data Format

The basis of the NCOUNTER® Analysis system is the unique code assigned to each gene to be assayed (International Patent Application No. PCT/US2008/059959 and Geiss et al. Nature Biotechnology. 2008. 26(3): 317-325; the contents of which are each incorporated herein by reference in their entireties). The code is composed of an ordered series of colored fluorescent spots which create a unique barcode for each target to be assayed. A pair of probes are designed for each target, a biotinylated capture probe and a reporter probe carrying the fluorescent barcode.

Specific reporter and capture probes are synthesized for each target. Briefly, sequence-specific DNA oligonucleotide probes are attached to code-specific reporter molecules. Capture probes are made by ligating a second sequence-specific DNA oligonucleotide for each target to a universal oligonucleotide containing biotin. Reporter and capture probes are all pooled into a single hybridization mixture, the "probe library".

The expression levels of all targets are measured in a single multiplexed hybridization reaction. The sample is combined with the probe library, and hybridization occurs in solution. After hybridization, the tripartite hybridized complexes are purified in a two-step procedure using magnetic beads linked to oligonucleotides complementary to universal sequences present on the capture and reporter probes. This dual purification process allows the hybridization reaction to be driven to completion with a large excess of target-specific probes, as they are ultimately removed, and, thus, do not interfere with binding and imaging of the sample. All post hybridization steps are handled robotically on a custom liquid-handling robot (Prep Station, NanoString Technologies).

Purified reactions are deposited by the Prep Station into individual flow cells of a sample cartridge, bound to a streptavidin-coated surface via the capture probe, electrophoresed to elongate the reporter probes, and immobilized. After processing, the sample cartridge is transferred to a fully automated imaging and data collection device (Digital Analyzer, NanoString Technologies). The expression level of a target is measured by imaging each sample and counting the number of times the code for that target is detected. For each sample, typically 600 fields-of-view (FOV) are imaged (1376×1024 pixels) representing approximately 10 mm$^2$ of the binding surface. Typical imaging density is 100-1200 counted reporters per field of view depending on the degree of multiplexing, the amount of RNA, and overall target expression levels. Data is output in simple spreadsheet format listing the number of counts per target, per sample. NCOUNTER® miRNA Expression Assay Sample Preparation Protocol In the NCOUNTER® miRNA Expression Assay, the miRNA samples must be tagged before they can be introduced into the probe hybridization reaction of the NCOUNTER® Analysis System described above. Unless otherwise noted, the data in the examples provided were generated using an embodiment of the NCOUNTER® miRNA Expression Assay Kit Sample Preparation Protocol described below, followed by the standard NCOUNTER® Assay Protocol described briefly above and in Geiss et al.

Figure 4:
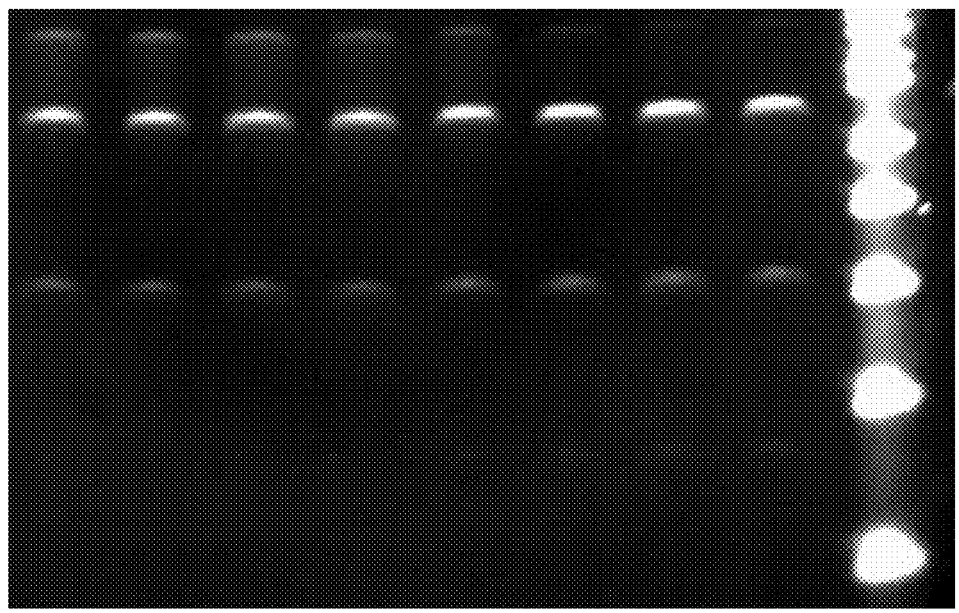
FIG. 4 is a photograph of a gel electrophoresis assay. The results of successful ligation reactions completed at temperatures ranging from 45-52° C. and containing miRNAs, tags and the corresponding bridges are shown.
Figure 5A:
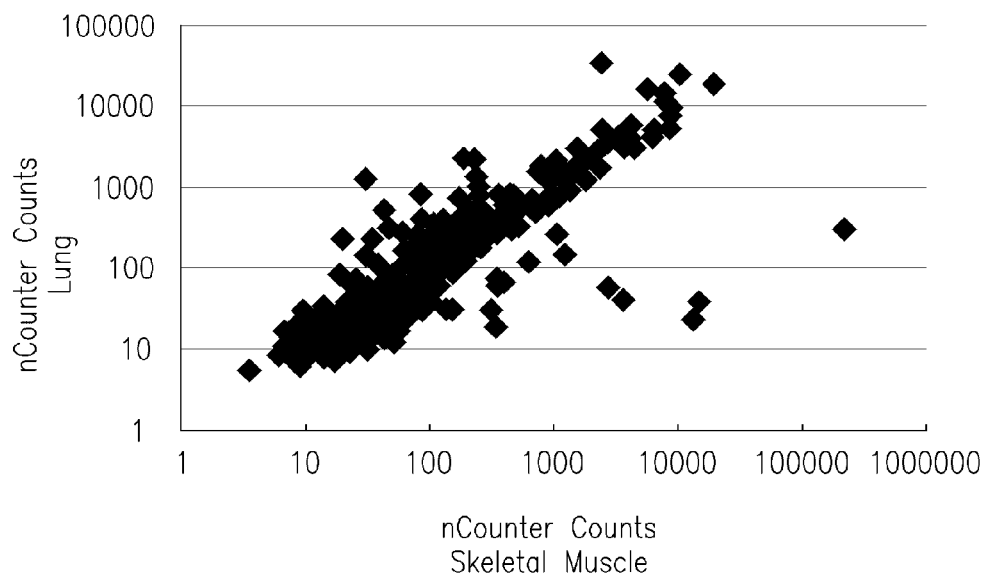
FIG. 5A is a graph depicting miRNA expression levels in total RNA isolated from skeletal muscle versus total RNA isolated from lung tissue. Samples were measured using the NCOUNTER® miRNA Expression Assay Kit.
Figure 5B:
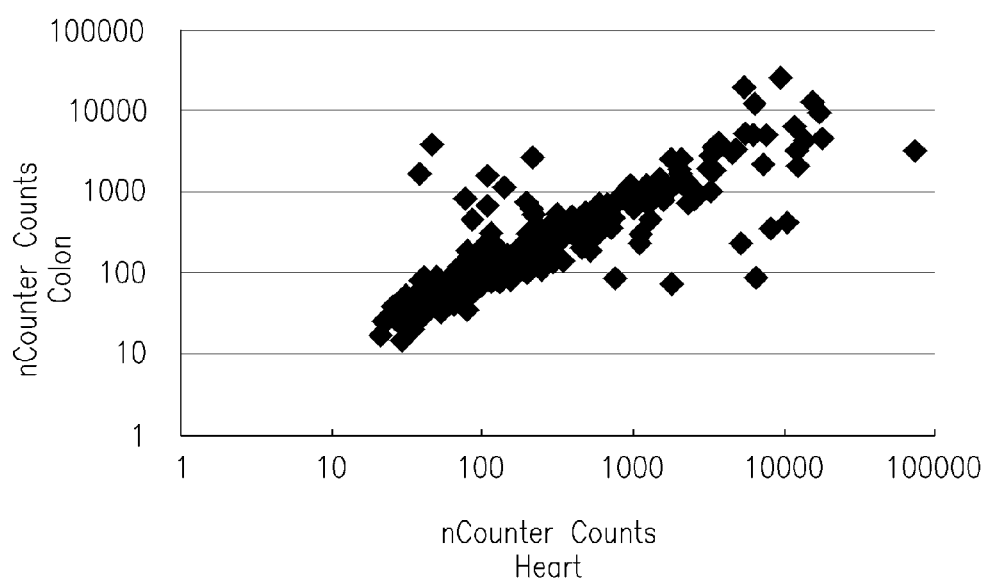
FIG. 5B is a graph depicting miRNA expression levels in total RNA isolated from heart tissue versus total RNA isolated from colon tissue. Samples were measured using the NCOUNTER® miRNA Expression Assay Kit.
Figure 5C:
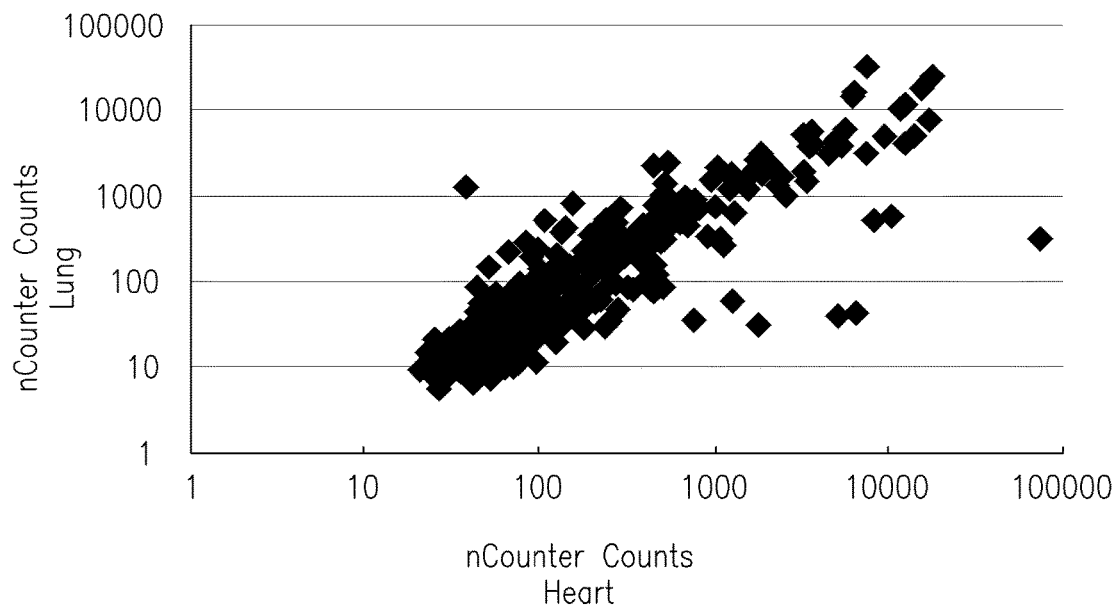
FIG. 5C is a graph depicting miRNA expression levels in total RNA isolated from heart tissue versus total RNA isolated from lung tissue. Samples were measured using the NCOUNTER® miRNA Expression Assay Kit.
Figure 5D:
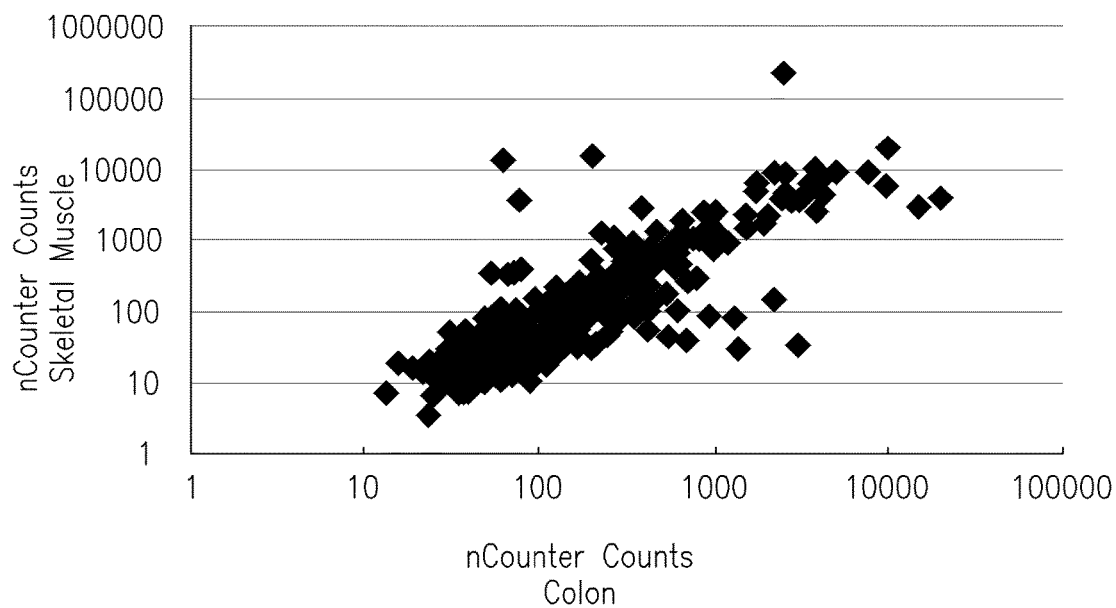
FIG. 5D is a graph depicting miRNA expression levels in total RNA isolated from colon tissue versus total RNA isolated from skeletal muscle. Samples were measured using the NCOUNTER® miRNA Expression Assay Kit.

Annealing buffer (200 mM Tris, 750 mM KCl) was mixed with a tag pool. The tag pool includes 60 nM each of a set of the synthetic DNA oligonucleotides (Integrated DNA Technologies, Coralville, Iowa) similar to those described in Table 2. The exact composition of this pool depends on the specific miRNAs being measured. An equivalent amount of a bridge pool is added to the mixture. The bridge pool consists of 55 nM each of a set of synthetic DNA oligonucleotides (Integrated DNA Technologies) similar to those described in Table 3. The exact composition of this pool depended on the specific miRNAs being measured, and matched the profile of the tag pool. 100 ng of total RNA or a defined amount of synthetic RNA target (Integrated DNA Technologies) is added and DEPC-treated water (Ambion, Austin, Tex.) was added to normalize the volume of each reaction. Samples were denatured and annealed in a thermocycler (BioRad, Hercules, Calif.) ° C. An equal-parts mixture of 50% PEG-4000 (CalBioChem/EMD Biosciences, San Diego, Calif.) and T4 DNA Ligase buffer (Enzymatics, Beverly, Mass.) was prepared for addition. Samples were briefly removed from the thermocycler, PEG/ligase buffer stock solution was added to each tube, and samples were mixed and spun down. Tubes were returned to the thermocycler and T4 DNA Ligase (Enzymatics) was added directly to the samples without removing them from the thermocycler. All thermocycler reactions were performed at temperatures in the range of 45-50° C. (FIG. 4).

Lambda Exonuclease (Enzymatics) was added to each sample at room temperature. Samples were incubated at 37° C. for 2 hours, heat-inactivated at 70° C. and chilled. DEPC diluted sample was used as the substrate in a standard NCOUNTER® hybridization reaction using a Codeset for miRNA detection (NanoString Technologies, Seattle, Wash.), following the manufacturer's instructions.

Loading of ligase should take approximately 6 minutes per 24 samples. Direct addition of ligase to the reaction tubes on the heat block at 48° C. is a critical step. Failure to do so will result in decreased assay performance, especially in terms of assay specificity.

The denaturing, annealing, ligation, and purification reactions described herein may be performed within a broader range of temperatures that span, for example, from 37-95° C. Specifically, the denaturing, annealing, ligation, and purification reactions described herein are performed with one or more of the following ranges including, but limited to, 37-45° C., 44-53° C., 45-52° C., 45-50° C., 50-55° C., 55-60° C., 65-70° C., 70-75° C., 75-80° C., 85-90° C., and 90-95° C. Alternatively, the denaturing, annealing, ligation, and purification reactions described herein are performed with one or more of the following ranges including, but limited to, 37-45° C., 37-50° C., 37-55° C., 37-60° C., 37-65° C., 37-70° C., 37-75° C., 37-80° C., 37-85° C., 37-90° C., and 37-95° C.

NCOUNTER® In the examples below, the data from the assays is represented as the number of counts detected in 600 fields-of-view by the NCOUNTER® Analysis System. The number of counts correlates with the expression level of the target RNA.

Below, exemplary tag and bridge sequences appropriate for detection of corresponding mrRNAs in Table 1 are shown.

TABLE 2

Exemplary Tag Sequences

| miRNA | Tag Sequence | SEQ ID NO: |
|---|---|---|
| hsa-let-7a | GGGCTTGACATCGGCGACACAAAATGCTTCTAACTCGCTGTGAAT | 11 |
| hsa-let-7b | GGGATATATTCCTTTTTTTTGCAATTAAACTGCCCAGGCGATCTGTTG | 12 |

TABLE 2-continued

Exemplary Tag Sequences

| miRNA | Tag Sequence | SEQ ID NO: |
|---|---|---|
| hsa-let-7c | GCTGCGTAGTTTATCTGCATCACTCGTACTGAAATGCTCACA | 13 |
| hsa-let-7d | GGAGTAGTTTGTCCTTCTGGAATTTCTTCCTTTGATTTTGCCATTTT | 14 |
| hsa-let-7e | GTCGAAGTCCTTCGAGTGCATGAGCTGTCTTTCACATGATACATCG | 15 |
| hsa-let-7f | GGTGGGGCTTGTCGACTGATAGTAACTGTGGTTCGAGTTATGCG | 16 |
| hsa-let-7g | GACGGTCCTAGAAGTCAAAAAGCTGCTTGATCGAAAAAAAGCAG | 17 |
| hsa-let-7i | GGTTTTAATAGCGCGAGAACAAGTGAGACGTGTATAGTTGCCATGCTG | 18 |
| hsa-miR-1 | GCCGTGACCCAACTCTATTCCCATTGCCTCCAAACCAGCCCTTG | 19 |
| hsa-miR-100 | GAAAAATAAAAAGTAAATTGGGCAATACCACCAAAATCGTTCTTTATGGGGT | 20 |

TABLE 3

Exemplary Bridge Sequences

| miRNA | Bridge Sequence | SEQ ID NO: |
|---|---|---|
| hsa-let-7a | TGTCAAGCCCAACTATACAACCTACTAC | 21 |
| hsa-let-7b | AAGGAATATATCCCAACCACACAACCTAC | 22 |
| hsa-let-7c | ACTACGCAGCAACCATACAACCTACT | 23 |
| hsa-let-7d | GACAAACTACTCCAACTATGCAACCTACT | 24 |
| hsa-let-7e | AGGACTTCGACAACTATACAACCTCC | 25 |
| hsa-let-7f | AGCCCCACCAACTATACAATCTACTACC | 26 |
| hsa-let-7g | CTAGGACCGTCAACTGTACAAACTACTACC | 27 |
| hsa-let-7i | CGCTATTAAAACCAACAGCACAAACTACTAC | 28 |
| hsa-miR-1 | GGTCACGGCATACATACTTCTTTACATT | 29 |
| hsa-miR-100 | TTTACTTTTTATTTTTCCACAAGTTCGGATCT | 30 |

Bridge and Tag Design

The addition of a specific nucleic acid tag to the small RNA target serves two main purposes: 1) it adds a robust, unique identifier to each RNA species, making it easier to discriminate between closely-related RNA targets in a hybridization-based assay; and 2) it allows for the manipulation and equalization of the functional $T_m$'s of the targets so that hybridization assays for different RNA targets can be multiplexed at the same temperature.

To avoid cross-hybridization, which would lead to false positive signals, the tag sequence should be unrelated to any other sequence in the transcriptome of the organism from which the small RNA target sequences are derived. Optimally, the tag sequence will be unrelated to the transcriptome of any known organism, so that the same tags can be used to generate an NCOUNTER® Small RNA Preparation Assay Kit for any organism. Cross-hybridization avoidance was achieved by using novel sequences from the External RNA Controls Consortium (ERCC) database as a starting point for generating the tag sequences.

For ease of synthesis, the nucleic acid tags were designed as DNA oligonucleotides, which were covalently ligated onto the 3' end of each RNA, forming a chimeric RNA-DNA target for detection. The detection assay, based on NanoString's NCOUNTER® Analysis System, relies on the hybridization of two adjacent probes, each with a $T_m$ of 76° C. to 84° C., to the target. The final RNA-DNA chimeric target was designed to comprise two regions, a reporter attachment region and a capture attachment region, each with a $T_m$ of approximately 76° C. to 84° C.

The ligation of the tags must be highly specific, both individually and in a multiplexed setting. This specificity is achieved through the individual design of DNA oligonucleotide bridges which anneal in a sequence-specific manner to the small RNA at one end and the specific tag at the other end (FIG. 2), bringing the RNA and its assigned tag together in close proximity, allowing for a ligation event to form a covalent bond between the two. The ability to multiplex the ligations of hundreds of different species of small RNAs to their respective tags was achieved by careful design of the bridge and tag sequences based on calculations of the $T_m$'s of the bridge/RNA/tag interactions so that all of the bridges anneal specifically to their target RNAs and tags within a narrow temperature range, with calculated $T_m$'s of between 44° C. and 53° C. An example of these trimmed sequences is shown in Table 4.

All DNA/DNA $T_m$ calculations were done using the methods described in Allawi H. T., SantaLucia J. (1997) Thermodynamics and NMR of internal G-T mismatches in DNA. *Biochemistry* 36: 10581-10594 and SantaLucia J. Jr, Allawi H. T., Seneviratne P. A. (1996). Improved nearest-neighbor parameters for predicting DNA duplex stability. *Biochemistry* 35: 3555-3562.

All RNA/DNA $T_m$ calculations were done using the methods described in Sugimoto N., Nakano S., Katoh M., Matsumura A., Nakamuta H., Ohmichi T., Yoneyama M., Sasaki M. (1995). Thermodynamic parameters to predict stability of RNA/DNA hybrid duplexes, *Biochemistry* 34: 11211-11216 and SantaLucia J. Jr, Allawi H. T., Seneviratne P. A. (1996) Improved nearest-neighbor parameters for predicting DNA duplex stability, *Biochemistry* 35: 3555-3562). Note that the adjustments for the $Na^+$ concentration in the DNA/RNA calculations were done using the DNA duplex coefficients in SantaLucia et al.

Tag and Bridge Design

A starting pool of sequence was generated by selecting sequences from the External RNA Controls Consortium (ERCC) database of sequences available online.

Figure 2:
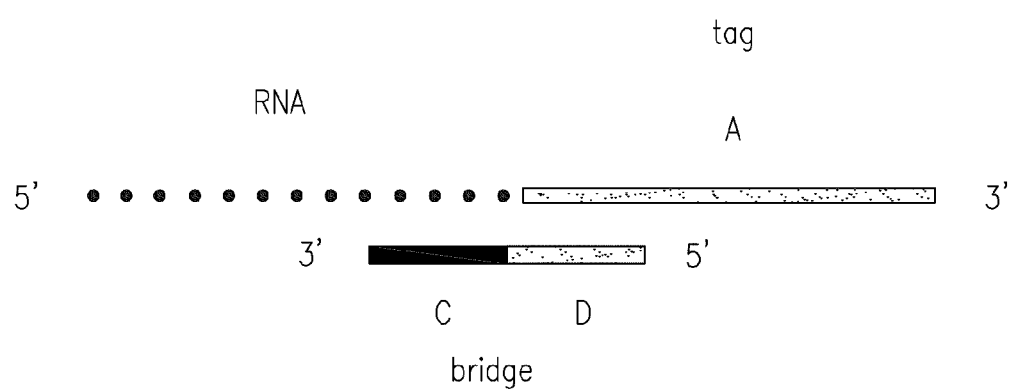
FIG. 2 is a schematic representation of the chimeric RNA:DNA heteroduplex, where the reporter attachment region (A) comprises the DNA tag and the DNA sequences (C) and (D) comprise the bridge.
Figure 3:
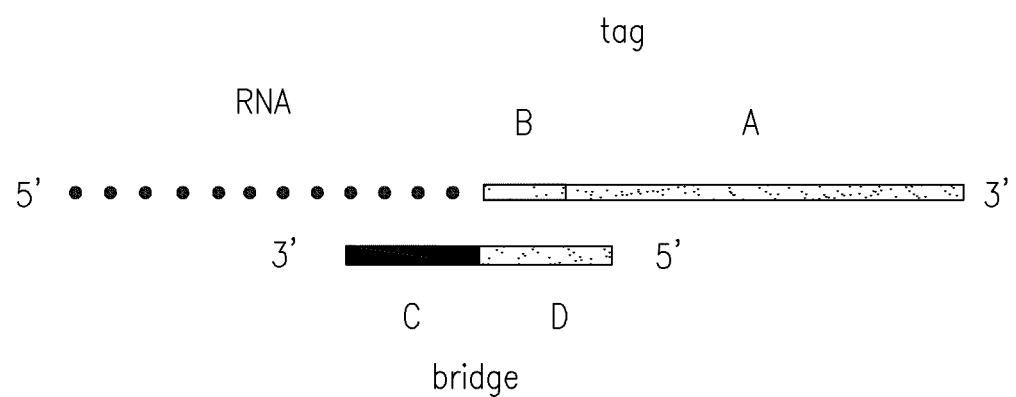
FIG. 3 is a schematic representation of the chimeric RNA:DNA heteroduplex, where the reporter attachment region (A) and an additional sequence (B) comprise the DNA tag and the DNA sequences (C) and (D) comprise the bridge.

These sequences were then processed by dividing them into 35-base regions and calculating their predicted $T_m$'s. A 'reporter attachment pool' was created of 35-base sequences with a DNA/DNA $T_m$ between 76° C. and 84° C. A second 'general pool' was created from the remaining sequences of random lengths. For each short RNA sequence (shown as a dotted line in FIGS. 2 and 3), a 35-base sequence was arbitrarily selected from the reporter attachment pool and assigned as the reporter attachment region (FIGS. 2-3, fragment A). The reverse complement of the small RNA, the RNA-RC sequence, was generated, and the predicted RNA/DNA $T_m$ of a duplex in which the RNA-RC was the DNA strand was calculated. Based on the outcome of this calculation, the tag and bridge design for each specific small RNA sequence was assigned to one of two design strategies, Type 1 or Type 2.

Type 1 Design.

Type 1 tag and bridge design is pictured in FIG. 2. If the calculated RNA/DNA $T_m$ of the RNA-reverse complement DNA duplex (RNA-RC DNA duplex) was between 76° C. and 84° C., then fragment A in FIG. 2 defined the full-length tag and the short RNA sequence (for example the miRNA sequence) defined the capture attachment region. The bridge sequence (FIG. 2, fragments C+D) was subsequently calculated in 2 parts: the small RNA bridge segment (C) and the tag bridge segment (D). The small RNA bridge segment was generated by taking the RNA-RC DNA sequence and identifying the fragment of sequence at the 5'-most end with a calculated RNA/DNA $T_m$ of between 44° C. and 53° C. The tag bridge segment was generated by taking the reverse complement of the reporter attachment region (A) and identifying the fragment of sequence at the 3'-most end with a calculated DNA/DNA $T_m$ of between 44° C. and 53° C. The full bridge sequence was created by joining the 5' end of the small RNA bridge segment to the 3' end of the tag bridge segment (C+D).

Type 2 Design

Type 2 tag and bridge design is pictured in FIG. 3. If the calculated $T_m$ of the RNA-RC DNA duplex was below 76° C., then an additional segment of DNA sequence of random size was selected from the general pool sequences, added to the 5' end of the RNA-RC, and the predicted DNA/DNA $T_m$ of this combined sequence was calculated. The actual duplex this portion forms in the final hybridization assay is a DNA/RNA-DNA-chimera duplex, but the calculation was simplified to reflect a DNA/DNA interaction. This process was repeated until a sequence combination with a predicted DNA/DNA $T_m$ between 76° C. and 84° C. was found. This additional segment of sequence is shown as segment B in FIG. 3. The full-length tag was then created by joining B to the 5' end of A (FIG. 3). The small RNA sequence combined segment B defined the capture attachment region.

The bridge sequence (C+D, FIG. 3) was calculated in 2 parts: the small RNA bridge segment (C) and the tag bridge segment (D, FIG. 3). The small RNA bridge segment was generated in an identical manner as that described in the Type 1 design above. The tag bridge segment was generated by taking the reverse complement of the Type 2 tag sequence (B+A, FIG. 3) and identifying the fragment of sequence at the 3'-most end with a calculated DNA/DNA $T_m$ of between 44° C. and 53° C. The full bridge sequence was created by joining the 5' end of the small RNA bridge segment to the 3' end of the tag bridge segment (C+D).

TABLE 4

Trimming Sequences

| miRNA Name | Trimmed Sequence | Length | Tm (RNA:DNA) |
|---|---|---|---|
| let-7a | GUAGUAGGUUGUAUAGUU (SEQ ID NO: 31) | 18 | 48.6753 |
| let-7b | GUAGGUUGUGUGGUU (SEQ ID NO: 32) | 15 | 49.7397 |
| let-7c | AGUAGGUUGUAUGGUU (SEQ ID NO: 33) | 16 | 50.4865 |
| let-7d | AGUAGGUUGCAUAGUU (SEQ ID NO: 34) | 16 | 50.5324 |
| let-7e | GGAGGUUGUAUAGUU (SEQ ID NO: 35) | 15 | 48.3192 |

Alien DNA Sequences

The term "alien DNA sequence" describes a randomized DNA sequence that has minimal or negligible cross-reactivity with any known genome. The homology and/or identity of a candidate alien DNA sequence is compared to all known sequences in a particular species or all species by, for example, using the NBLAST and BLAST programs of Altschul, et al. (J. Mol. Biol. 215:403-10 (1990)). Alien DNA sequences do not encode genes or regulatory elements thereof. Rather, the alien DNA sequences have non-coding functions within the compositions, methods, and kits of the invention.

Alien DNA sequences are used within the compositions, methods, and kits of the invention to minimize or prevent interactions (e.g. hybridization) between molecules that contain alien DNA sequences and molecules that are isolated from a target sample, genome, cell, animal, or extract thereof (e.g. target RNA molecules, non-corresponding bridges, non-corresponding tags, non-corresponding reporter molecules). Target RNA molecules and the corresponding bridges, and tags share either partial or complete sequence complementarity, whereas target RNA molecules do not share either partial or complete sequence complementarity with non-corresponding bridges or tags. Reporter molecules and the corresponding tags share either partial or complete sequence complementarity, whereas reporter molecules do not share either partial or complete sequence complementarity with non-corresponding tags.

Tag molecules, reporter molecules, and bridge molecules contain alien DNA sequences. The alien DNA molecules contained within a tag and a corresponding bridge specifically hybridize to each other, and optimally, to no other molecule present in the composition during the denaturing, annealing, ligation, and/or purification reaction. Alternatively, the alien DNA molecules contained within a tag and a corresponding bridge specifically hybridize to each other, and preferably, have a lower than 15% homology across 35-50 bases with a maximum continuous homology of 15 bases or less to the other molecules present in the composition during the denaturing, annealing, ligation, and/or purification reaction. A reporter molecule containing an alien DNA sequence may specifically hybridize to the corresponding tagged miRNA molecule following the purification reaction, and optimally, to no other molecule present in the composition. Alternatively, a reporter molecule containing an alien DNA sequence may specifically hybridize to the corresponding tagged miRNA molecule following the purification reaction, and preferably, have a lower than 15% homology across 35-50 bases with a maximum continuous homology of 15 bases or less to the other molecules present in the composition.

Exemplary alien DNA sequences encompassed by the invention have no greater than 85% identity across 35-50 bases with a maximum continuous homology of 15 bases or less to any known genomic DNA or RNA sequence. Moreover, the alien DNA has no greater than 85% identity across 35-50 bases with a maximum continuous homology of 15 bases or less to any known DNA or RNA sequence from or transcribed by a genome from which a target RNA molecule is transcribed. Target RNA molecules are from or transcribed by the genomes of any species, including, but not limited to, animals, plants, bacteria, fungi and viruses. Preferred species from which target RNA molecules are derived include mammals, and most preferably include humans, primates, and mice.

Alien DNA sequences have a lower than 15% homology across 35-50 bases with a maximum continuous homology of 15 bases or less to all known DNA and RNA molecules. Specifically, alien DNA sequences have a homology of less than 15% across 35-50 bases with a maximum continuous homology of 15 bases or less to all the DNA and RNA molecules in a composition or kit. Specifically, the alien DNA sequence has a lower than 15%, 10%, 5%, 2%, 1% or any percentage point in between, homology across 35-50 bases, with a maximum continuous homology of 15 bases or less of DNA and RNA molecules in a composition or kit.

Alien DNA sequences may hybridize to a portion of a bridge that contains DNA, or specifically, alien DNA. Specifically, the alien DNA sequence have a lower than 15%, 10%, 5%, 2%, 1% or any percentage point in between, homology across 35-50 bases with a maximum continuous homology of 15 bases or less with any DNA and RNA molecules in the composition other than the third DNA sequence of the bridge.

Nucleic Acid Molecules

The invention provides bridges and tags, e.g. isolated and purified nucleic acid molecules that bind small RNA molecules, including miRNA molecules. Exemplary tag molecules include, but are not limited to, those deoxyribonucleic acid molecules of SEQ ID NOs: 11-20. Exemplary bridge molecules include, but are not limited to, those deoxyribonucleic acid molecules of SEQ ID NOs: 21-30.

In other aspects of the invention, isolated nucleic acid molecules, such as RNA molecules and DNA bridges and tags, bind sequences containing one or more insertions, deletions, inversions, frameshifts, translocations, recombinations, or substitutions.

The isolated nucleic acid molecules of the present invention include single- and double-stranded ribonucleic acid (RNA) and deoxyribonucleic acid (DNA) molecules, as well as all art-recognized analogs, derivatives, or hybrid molecules thereof. Isolated nucleic acid molecules of the present invention also include reagents for synthesizing RNA molecules, bridges, and tags, such as isolated full-length genes, transcripts, cDNA molecules, primers, vectors, plasmids, endogenous or naturally-occurring RNA molecules, bridges, tags, and fragments thereof.

Isolated nucleic acid molecules of the invention are engineered to bind RNA sequences, DNA, or "alien" DNA sequences that are distinct from most other nucleic acids present in the natural source of the nucleic acid molecule. Moreover, an "isolated" nucleic acid molecule can be substantially free of other cellular material, or culture medium when produced by recombinant techniques, or chemical precursors or other chemicals when chemically synthesized.

A nucleic acid molecule can be fused to other coding or regulatory sequences and still be considered "isolated". Nucleic acid molecules present in nonhuman transgenic animals, which do not naturally occur in the animal, are also considered "isolated". For example, recombinant nucleic acid molecules contained in a vector are considered "isolated". Further examples of "isolated" nucleic acid molecules include recombinant DNA or RNA molecules maintained in heterologous host cells, and purified (partially or substantially) DNA or RNA molecules in solution. Isolated RNA molecules include in vivo or in vitro RNA transcripts of the isolated nucleic acid molecules of the present invention. Moreover, isolated RNA molecules include, but are not limited to, transfer RNA (tRNA), small nucleolar RNA (snoRNA), microRNA (miRNA), a short interfering RNA (siRNA), short hairpin RNA (shRNA), repeat associated small interfering RNA (rasiRNA), and piwi-interacting RNA (piRNA). Isolated nucleic acid molecules according to the present invention further include such molecules produced synthetically.

Generally, an isolated nucleic acid molecule comprises one or more sequences engineered to bind to a RNA molecule, bridge, or tag, with flanking nucleotide sequences on either side of the target RNA, bridge, or tag sequence. A flanking sequence can include nucleotide residues that are naturally associated with the targeted RNA, bridge or tag and/or heterologous nucleotide sequences. Preferably the flanking sequence is up to about 500, 300, 100, 60, 50, 30, 25, 20, 15, 10, 8, or 4 nucleotides (or any other length in-between) on either side of the target RNA, bridge, or tag sequence, or as long as the full-length gene, entire coding, or non-coding sequence (or any portion thereof, such as, an exon, intron, or a 5' or 3' untranslated region).

As used herein, the term "fragment" is meant to describe an isolated nucleic acid molecule that is shorter the isolated nucleic acid molecule from which it is derived. Fragments of isolated nucleic acid molecules of the invention can contain, consist of, or comprise any part of the isolated nucleic acid molecule from which it is derived. A fragment typically comprises a contiguous nucleotide sequence at least about 8 or more nucleotides, more preferably at least about 10 or more nucleotides, and even more preferably at least about 15 or more nucleotides. Further, a fragment could comprise at least about 8, 10, 15, 20, 25, 30, 35, 40, 45, 50, 55, 60, 65, 70, 75, 80, 85, 90, 95, 100, 250 or 500 (or any other number in-between) nucleotides in length. The length of the fragment will be based on its intended use. A labeled probe can then be used, for example, to screen a cDNA library, genomic DNA library, or mRNA to isolate nucleic acid corresponding to the region of interest. Further, primers and probes can be used in amplification reactions, such as for purposes of assaying RNA or miRNA genes, cross-reactivity of RNA molecules with bridges or tags, homology of RNA molecules with bridge or tag sequences, identity RNA molecules with bridge or tag sequences, or for cloning specific regions of a RNA molecule or gene, bridge molecule, or tag molecule.

An isolated nucleic acid molecule of the present invention further encompasses a RNA molecule, bridge or tag that is the product of any one of a variety of nucleic acid amplification methods, which are used to increase the copy numbers of a polynucleotide of interest in a nucleic acid sample. Such amplification methods are well known in the art, and they include but are not limited to, polymerase chain reaction (PCR) (U.S. Pat. Nos. 4,683,195; and 4,683,202; PCR Technology: Principles and Applications for DNA Amplification, ed. H. A. Erlich, Freeman Press, NY, N.Y., 1992), ligase chain reaction (LCR) (Wu and Wallace, Genomics 4:560, 1989; Landegren et al., Science 241:1077, 1988), strand displacement amplification (SDA) (U.S. Pat. Nos. 5,270,184; and 5,422,252), transcription-mediated amplification (TMA) (U.S. Pat. No. 5,399,491), linked linear amplification (LLA) (U.S. Pat. No. 6,027,923), and the like, and isothermal amplification methods such as nucleic acid sequence based amplification (NASBA), and self-sustained sequence replication (Guatelli et al., Proc. Natl. Acad. Sci. USA 87: 1874, 1990). Based on such methodologies, a person skilled in the art can readily design primers in any suitable regions 5' and 3' to a RNA molecule or gene disclosed herein. Moreover, amplification methods include synthesizing in silico a RNA molecule, bridge, or tag described herein.

As used herein, an "amplified polynucleotide" of the invention is an isolated nucleic acid molecule in which the number of molecules has been increased at least two-fold by any nucleic acid amplification method performed in vitro as compared to its starting amount in a test sample. In other preferred embodiments, an amplified polynucleotide is the result of at least ten-fold, fifty-fold, one-hundred fold, one-thousand fold, or even ten-thousand fold increase as compared to its starting amount in a test sample. Generally, an amplified polynucleotide is at least about 10 nucleotides in length. More typically, an amplified polynucleotide is at least about 15 nucleotides in length. In a preferred embodiment of the invention, an amplified polynucleotide is at least about 20-25 nucleotides in length. In a more preferred embodiment of the invention, an amplified polynucleotide is at least about 20, 25, 30, 35, 40, 45, 50, or 100 nucleotides, or any value in between, in length. In yet another preferred embodiment of the invention, an amplified polynucleotide is at least about 100, 200, or 300 nucleotides, or any value in between in length. While the total length of an amplified polynucleotide of the invention can be as long as an exon, an intron, a 5' UTR, a 3' UTR, or the entire gene where the RNA molecule of interest resides, an amplified product is typically no greater than about 1,000 nucleotides in length (although certain amplification methods may generate amplified products greater than 1000 nucleotides in length).

In one embodiment, the invention provides nucleic acid molecules that comprise, consist essentially of, or consist of, for example, the nucleotide sequences of SEQ ID NOs: 1-35. The techniques described herein may be used to provide an unlimited number and variation of nucleic acid molecules to be used in the assay to enable detection. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleotide residues, such as residues that are naturally associated with it or heterologous nucleotide sequences. Such a nucleic acid molecule can have one to a few additional nucleotides or can comprise many more additional nucleotides. A nucleic acid molecule consists essentially of a nucleotide sequence when the final nucleic acid molecule contains the nucleic acid sequence and only regulatory or maintenance sequences. Regulatory and maintenance sequences are those sequences that allow the nucleotide sequence to be expressed and/or translated. A nucleic acid molecule comprises a nucleotide sequence when the final nucleotide sequence of the nucleic acid molecule contains only that nucleic acid sequence. A brief description of how various types of these nucleic acid molecules can be readily made and isolated is provided below, and such techniques are well known to those of ordinary skill in the art (Sambrook and Russell, 2000, Molecular Cloning: A Laboratory Manual, Cold Spring Harbor Press, NY).

Isolated nucleic acid molecules can be in the form of RNA, such as mRNA or miRNA, or in the form DNA, including cDNA and genomic DNA, which may be obtained, for example, by molecular cloning or produced by chemical synthetic techniques or by a combination thereof (Sambrook and Russell, 2000, Molecular Cloning: A Laboratory Manual, Cold Spring Harbor Press, NY). Furthermore, isolated nucleic acid molecules can also be partially or completely in the form of one or more types of nucleic acid analogs, such as peptide nucleic acid (PNA) (U.S. Pat. Nos. 5,539,082; 5,527,675; 5,623,049; 5,714,331). The nucleic acid, especially DNA, can be double-stranded or single-stranded. Single-stranded nucleic acid can be the coding strand (sense strand) or the complementary non-coding strand (anti-sense strand). DNA, RNA, or PNA segments can be assembled, for example, from fragments of the human genome or any genome including alien sequences (in the case of DNA or RNA) or single nucleotides, short oligonucleotide linkers, or from a series of oligonucleotides, to provide a synthetic nucleic acid molecule. Nucleic acid molecules can be readily synthesized using the sequences provided herein as a reference; oligonucleotide and PNA oligomer synthesis techniques are well known in the art (see, e.g., Corey, "Peptide nucleic acids: expanding the scope of nucleic acid recognition", Trends Biotechnol. 1997 June; 15(6):224-9, and Hyrup et al., "Peptide nucleic acids (PNA): synthesis, properties and potential applications", Bioorg Med. Chem. 1996 January; 4(1):5-23). Furthermore, large-scale automated oligonucleotide/PNA synthesis (including synthesis on an array or bead surface or other solid support) can readily be accomplished using commercially available nucleic acid synthesizers, such as the Applied Biosystems (Foster City, Calif.) 3900 High-Throughput DNA Synthesizer or Expedite 8909 Nucleic Acid Synthesis System, and the sequence information provided herein.

The present invention encompasses nucleic acid analogs that contain modified, synthetic, or non-naturally occurring nucleotides or structural elements or other alternative/modified nucleic acid chemistries known in the art. Such nucleic acid analogs are useful, for example, as detection reagents (e.g., primers/probes). Furthermore, kits/systems (such as beads, arrays, etc.) that include these analogs are also encompassed by the present invention. For example, PNA oligomers that are based on the polymorphic sequences of the present invention are specifically contemplated. PNA oligomers are analogs of DNA in which the phosphate backbone is replaced with a peptide-like backbone (Lagrifoul et al., Bioorganic & Medicinal Chemistry Letters, 4: 1081-1082 (1994), Petersen et al., Bioorganic & Medicinal Chemistry Letters, 6: 793-796 (1996), Kumar et al., Organic Letters 3(9): 1269-1272 (2001), WO96/04000). PNA hybridizes to complementary RNA or DNA with higher affinity and specificity than conventional oligonucleotides and oligonucleotide analogs. The properties of PNA enable novel molecular biology and biochemistry applications unachievable with traditional oligonucleotides and peptides.

The term "isolated nucleic acid molecule" is not limited to molecules containing only naturally-occurring RNA or DNA, but also encompasses chemically-modified nucleotides and non-nucleotides. In certain embodiments, the isolated nucleic acid molecules lack 2'-hydroxy (2'-OH) containing nucleotides. Non-limiting examples of chemical modifications that are made in a RNA molecule, bridge, or tag, include without limitation phosphorothioate internucleotide linkages, 2'-deoxyribonucleotides, 2'-0-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation. These chemical modifications, when used in RNA molecules, bridges or tags, preserve function and increase the stability of these molecules.

Nucleotide and non-nucleotide linkers can be incorporated into RNA molecules, bridges and tags. A non-nucleotide linker may be comprised of an abasic nucleotide, polyether, polyamine, polyamide, peptide, carbohydrate, lipid, polyhydrocarbon, or other polymeric compounds (e.g., polyethylene glycols such as those having from 2 to 100 ethylene glycol units). Specific examples include those described by Seela and Kaiser, Nucleic Acids Res. 18:6353, 1990 and Nucleic Acids Res. 15:3113, 1987; Cload and Schepartz, J. Am. Chem. Soc. 113:6324, 1991; Richardson and Schepartz, J. Am. Chem. Soc. 113:5109, 1991; Ma, et al., Nucleic Acids Res. 21:2585, 1993 and Biochemistry 32:1751, 1993; Durand, et al., Nucleic Acids Res. 18:6353, 1990; McCurdy, et al., Nucleosides & Nucleotides 10:287, 1991; Jschke, et al., Tetrahedron Lett. 34:301, 1993; Ono, et al., Biochemistry 30:9914 (1991); Arnold, et al., International Publication No. WO 89/02439; Usman, et al., International Publication No. WO 95/06731; Dudycz, et al., International Publication No. WO 95/11910 and Ferentz and Verdine, J. Am. Chem. Soc. 113:4000, 1991. A "non-nucleotide" further means any group or compound that can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymidine, e.g., at the C1 position of the sugar.

Additional examples of nucleic acid modifications that improve the binding properties and/or stability of a nucleic acid include the use of base analogs such as inosine, intercalators (U.S. Pat. No. 4,835,263) and the minor groove binders (U.S. Pat. No. 5,801,115). Thus, references herein to nucleic acid molecules include PNA oligomers and other nucleic acid analogs. Other examples of nucleic acid analogs and alternative/modified nucleic acid chemistries known in the art are described in Current Protocols in Nucleic Acid Chemistry, John Wiley & Sons, N.Y. (2002). Isolated nucleic acids of the inventions are comprised of base analogs including, but not limited to, any of the known base analogs of DNA and RNA such as, but not limited to 4-acetylcytosine, 8-hydroxy-N-6-methyladenosine, aziridinylcytosine, pseudoisocytosine, 5-(carboxyhydroxylmethyl) uracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methyl guanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-Dmannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, 2,6-diaminopurine, and 2'-modified analogs such as, but not limited to 0-methyl, amino-, and fluoro-modified analogs.

In certain embodiments, the RNA molecules, bridges and tags of the invention are modified to enhance stability by modification with nuclease resistant groups, e.g., 2'-amino, 2'-C-allyl, 2'-fluoro, 2'-O-methyl, and 2'-H. (For a review see Usman and Cedergren, TIBS 17:34, 1992; Usman, et al., Nucleic Acids Symp. Ser. 31:163, 1994).

Chemically synthesizing nucleic acid molecules with modifications (base, sugar and/or phosphate) prevents their degradation by ribonucleases, which increases the efficiency of the assays described herein. See, e.g., Eckstein, et al., International Publication No. WO 92/07065; Perrault, et al., Nature 344:565, 1990; Pieken, et al., Science 253:314, 1991; Usman and Cedergren, Trends in Biochem. Sci. 17:334, 1992; Usman, et al, International Publication No. WO 93/15187; and Rossi, et al., International Publication No. WO 91/03162; Sproat, U.S. Pat. No. 5,334,711; Gold, et al., U.S. Pat. No. 6,300,074. All of the above references describe various chemical modifications that are made to the base, phosphate and/or sugar moieties of the isolated nucleic acid molecules described herein.

In one embodiment, the invention provides RNA molecules, bridges, and tags with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications, see Hunziker and Leumann, "Nucleic Acid Analogues: Synthesis and Properties, in Modern Synthetic Methods," VCH, 331-417, 1995, and Mesmaeker, et al, "Novel Backbone Replacements for Oligonucleotides, in Carbohydrate Modifications in Antisense Research," ACS, 24-39, 1994.

Further variants of the nucleic acid molecules including, but not limited to those identified as SEQ ID NOs: 1-35, such as naturally occurring allelic variants (as well as orthologs and paralogs) or synthetic variants produced by mutagenesis techniques, can be identified and/or produced using methods well known in the art. Such further variants can comprise a nucleotide sequence that shares at least 70-80%, 80-85%, 85-90%, 91%, 92%, 93%, 94%, 95%, 96%, 97%, 98%, or 99% sequence identity with a nucleic acid sequence disclosed as SEQ ID NOs: 1-35 (or a fragment thereof). Thus, the present invention specifically contemplates isolated nucleic acid molecule that have a certain degree of sequence variation compared with the sequences of SEQ ID NOs: 1-35.

The RNA molecules, bridges and tags of the invention are routinely made through techniques such as solid phase synthesis. Equipment for such synthesis is sold by several vendors including, for example, Applied Biosystems, (Foster City, Calif.). Any other means for such synthesis known in the art is additionally or alternatively employed. It is well known to use similar techniques to prepare oligonucleotides such as the phosphorothioates and alkylated derivatives.

Oligonucleotides are synthesized using protocols known in the art, e.g., as described in Caruthers, et al., Methods in Enzymology 211:3-19, 1992; Thompson, et al., International PCT Publication No. WO 99/54459; Wincott, et al., Nucleic Acids Res. 23:2677-2684, 1995; Wincott, et al., Methods Mol. Bio. 74:59, 1997; Brennan, et al., Biotechnol Bioeng. 61:33-45, 1998; and Brennan, U.S. Pat. No. 6,001,311. Synthesis of RNA molecules follows general procedures as described, e.g., in Usman, et al, J. Am. Chem. Soc. 109: 7845, 1987; Scaringe, et al., Nucleic Acids Res. 18:5433, 1990; and Wincott, et al., Nucleic Acids Res. 23:2677-2684, 1995; Wincott, et al., Methods Mol. Bio. 74:59, 1997.

The comparison of sequences and determination of percent identity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In a preferred embodiment, the percent identity between two amino acid sequences is determined using the Needleman and Wunsch algorithm (J. Mol. Biol. (48):444-453 (1970)) which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6.

In yet another preferred embodiment, the percent identity between two nucleotide sequences is determined using the GAP program in the GCG software package (Devereux, J., et al., Nucleic Acids Res. 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11-17 (1989)) which has been incorporated into the ALIGN program (version 2.0), using a PAM120 weight residue table, a gap length penalty of 12, and a gap penalty of 4.

The nucleotide and amino acid sequences of the present invention can further be used as a "query sequence" to perform a search against sequence databases to, for example, identify other family members or related sequences. Such searches can be performed using the NBLAST and BLAST programs (version 2.0) of Altschul, et al. (J. Mol. Biol. 215:403-10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (Nucleic Acids Res. 25(17):3389-3402 (1997)). When utilizing BLAST and gapped BLAST programs, the default parameters of the respective programs (e.g., BLAST and NBLAST) can be used. In addition to BLAST, examples of other search and sequence comparison programs used in the art include, but are not limited to, FASTA (Pearson, Methods Mol. Biol. 25, 365-389 (1994)) and KERR (Dufresne et al., Nat Biotechnol 2002 December; 20(12): 1269-71). For further information regarding bioinformatics techniques, see Current Protocols in Bioinformatics, John Wiley & Sons, Inc., N.Y.

Therapeutic Applications

Compositions and methods of the invention are used to detect gene expression in subjects who are at risk of developing an illness or disorder. Moreover, the compositions and methods of the invention are used to detect gene expression in subjects who have been diagnosed with an illness or disorder, and who are in need of a diagnosis or prognosis. The compositions and methods described herein are used to monitor disease progression and the effectiveness of therapy on the level of gene expression and regulation. Furthermore, the compositions and methods provided herein are used to screen individuals for their personal risk of developing a disorder as well as their risk of passing a disorder onto future children. Embryonic cells are tested using the compositions and methods of the invention for the presence or absence of disorders.

The invention can be used to determine the risk of developing a particular biological condition, a particular disease, such as a cancer, a genetic disorder, a developmental disorder, a degenerative disorder, a neurological disorder, a stem cell disorder, or other biological condition. Furthermore, the present invention can be used to monitor the progression of a disease or monitor responses to therapy. Specifically, the invention can be used to detect, to monitor progression of, or monitor therapeutic regimens for diseases of the heart, kidney, ureter, bladder, urethra, liver, prostate, heart, blood vessels, bone marrow, skeletal muscle, smooth muscle, various specific regions of the brain (including, but not limited to the amygdala, caudate nucleus, cerebellum, corpus callosum, fetal, hypothalamus, thalamus), spinal cord, peripheral nerves, retina, nose, trachea, lungs, mouth, salivary gland, esophagus, stomach, small intestines, large intestines, hypothalamus, pituitary, thyroid, pancreas, adrenal glands, ovaries, oviducts, uterus, placenta, vagina, mammary glands, testes, seminal vesicles, penis, lymph nodes, thymus, and spleen. The present invention can be used to detect, to monitor progression of, or monitor therapeutic regimens for a particular disease, such as a cancer, a genetic disorder, a developmental disorder, a degenerative disorder, a neurological disorder, a stem cell disorder, or other biological condition.

The methods of the invention encompass a variety of subjects, including mammals. In certain embodiments, the mammal is a human, non-human primate, mouse, rat, dog, cat, horse, or cow, but is not limited to these examples. Mammals other than humans are advantageously used as subjects that represent animal models of a particular disorder. The preferred subject is human. The methods of the invention also encompass a variety of subjects, including non-mammals. These include birds, reptiles, plants, bacteria, fungi, protists and viruses. Any sample containing naturally occurring or synthetic small RNA molecules may be used as the subject of the assay.

Cancer

Compositions and methods of the invention are used to identify cells and subjects at risk of developing or those cells and subjects who may have a predisposition for developing cancer. Moreover, the compositions and methods of the invention are used to differentiate cancer cell type, cancer subtype, tumor grade, or cancer stage for the purpose of diagnosing or prognosing a subject at risk of developing cancer or a subject who has developed cancer. The compositions and methods of the invention are further used to monitor to progression of a tumor, cancer, or a treatment regime. Additionally, the compositions and methods of the invention are used to screen individuals for any genetic predisposition to developing cancer.

The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

The compositions and methods of the invention are used to further determine cancer severity, as it is characterized by stage, tumor grade, and expression of factors that degrade the extracellular matrix, induce vascularization, inhibit cell adhesion and enable metastasis.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

Developmental and Degenerative Disorders

Compositions and methods of the invention are used to identify cells and subjects at risk of developing a developmental or degenerative disorder or those cells and subjects who may have a predisposition for developing a developmental or degenerative disorder. Moreover, the compositions and methods of the invention are used to differentiate developmental disorders, degenerative disorders, or developmental from degenerative disorders for the purpose of diagnosing or prognosing a subject at risk of presenting or a subject who has been diagnosed with a developmental or degenerative disorder. The compositions and methods of the invention are further used to monitor to progression of a developmental disorder, a degenerative disorder, or a treatment regime. Additionally, the compositions and methods of the invention are used to screen individuals for any genetic predisposition for presenting a developmental or degenerative disorder himself/herself, or for producing a child having a developmental or degenerative disorder.

The term "developmental disorder" includes any disorder that initially presents in an individual during gestation or early postnatal development. Early postnatal development encompasses a period of time from birth to age 18. Although developmental disorders are often considered synonymous with mental disabilities that cause mental, emotional, or cognitive deficits, the term "developmental disorder" is meant to encompass any disorder that presents in either a fetus or a child aged 18 years or less, regardless of the specific signs or symptoms associated with the disorder. Moreover, developmental disorders are typically characterized by an inadequate or malfunctioning development of biological or psychological process. Developmental disorders are also characterized by behavioral traits, family history, brain morphology, or genetic/biomarkers that are present during development and predict or indicate the individual's risk of developing the disease in adulthood (e.g. Huntington's Disease, Amyotrophic lateral sclerosis or ALS, and Schizophrenia).

A specific developmental disorder selectively affects one area of development, sparing essentially all other areas of development. Specific developmental disorders affect primarily hearing, vision, speech, or metabolism. However, a pervasive developmental disorder involves delays in the development of many basic skills, most notably the ability to socialize with others, because these conditions affect the child's ability to communicate and to use imagination. Pervasive developmental disorders include, but are not limited to, autism and autism spectrum disorders, Asperger's syndrome, childhood disintegrative disorder, Rett's Syndrome, attention-deficit disorder (ADD), and unspecified but pervasive disorders.

Exemplary developmental disorders also include, but are not limited to, Autism spectrum disorders (ASD), Angelman Syndrome, central auditory processing disorder (CAPD), cerebral palsy, Down Sydrome, expressive language disorder, Isopendric 15 (abbreviated idic(15)), Lanau-Kleffner Syndrome, neural tube defects, phenylketonuria (PKU), Prader-Willi Syndrome, seizure disorders, epilepsy, Tourette Syndrome, Williams Syndrome, hearing loss, deafness, blindness, vision impairment, jaundice/kernicterus, cluttering (speech disfluency), agnosias (visual, auditory, and somatosensory), anorexia nervosa disorder, acute stress disorder, adjustment disorder, bipolar disorder, body dysmorphic disorder, breathing-related sleep disorders, asthma, brief psychotic episode, bulimia nervosa, schizophrenia, Huntington's Disease (HD), multiple sclerosis (MS), amyotrophic lateral sclerosis (ALS), chronic motor or vocal tic disorder, circadian rhythm sleep disorder, conduct disorder, communication/language disorders, Cornelia de Lange Syndrome, fatal familial insomnia (FFI), Fahr's Syndrome (or idiopathic basal ganglia calcification), migraine, neoplasm (benign and malignant), Lupus erythematosus, autoimmune disorders, diabetes (type I), Wilson's Disease, Bell's Palsy, congenital heart disease, microcephaly, neonatal encephalitis, hydrocephalis, Parkinson's Disease, narcolepsy, muscular distrophy, Guillain-Barre Syndrome, neurofibromatosis, Von Hippel-Lindau Disease, dyslexia, familial hypercholesterolemia, polycystic kidney disease, hereditary spherocytosis, hereditary breast and ovarian syndrome, marfan syndrome, sickle cell anemia, sickle cell disease, cystic fibrosis, mucopolysaccharidoses, glycogen storage diseases, glactosemia, hemophilia, Androgenetic alopecia, Lebner's hereditary optic neuropathy, autoimmune disease, cleft palate, obesity, Gauchers Disease, Rett Syndrome, ataxia telagiectasia, long QT Syndrome, Alport Syndrome, male pattern baldness, SRY sex determination, achondroplasia, Cockayne syndrome, DiGeorge syndrome, fragile X syndrome, severe combined immunodeficiency, Waardenburg syndrome, Werner syndrome, Zellweger syndrome, adrenoleukodystrophy, glucose galactose malabsorption, hereditary hemochromatosis, Lesch-Nyhan syndrome, maple syrup urine disease, Menkes syndrome, Neimann-Pick syndrome, porphyria, Refsum disease, Tangier disease, Tay-Sachs disease, diastropic dysplasia, Ellis-van Creveld Syndrome (chondroectodermal dysplasia), paroxysmal nocturnal hemoglobinuria, thalassemia, Crohn's disease, Best disease, glaucoma, retinoblastoma, congenital adrenal hyperplasia, autoimmune polyglandular syndrome, multiple endocrine neoplasia, familial Mediterranean fever, immunodeficiency with hyper-IgM, Charcot-Marie-Tooth syndrome, fibrodysplasia ossificans progressive, myotonic dystrophy, essential tremor, Friedrich's Ataxia, spinal muscular atrophy, spinocerebellar ataxia, tuberous sclerosis, alpha-1-antitrypsin deficiency, and Pendred Syndrome.

The term "degenerative disorder" includes any disorder that initially presents in an adult individual. The term adult encompasses a period of time from age 18 to death. Although degenerative disorders are often considered synonymous with mental disabilities that cause mental, emotional, or cognitive deficits, the term "degenerative disorder" is meant to encompass any disorder that presents in an adult aged 18 years or older, regardless of the specific signs or symptoms associated with the disorder. Moreover, degenerative disorders are typically characterized by the deregulation or malfunction of an ordinarily operable biological or psychological process. Degenerative disorders can result from genetic predisposition, environmental factors, or exposure to pathogens such as a virus or prion.

Exemplary degenerative disorders include, but are not limited to, Alzheimer's Disease, dementia, senility, agnosias (visual, auditory, and somatosensory), acute stress disorder, adjustment disorder, bipolar disorder, body dysmorphic disorder, breathing-related sleep disorders (sleep apnea), brief psychotic episode, bulimia nervosa, schizophrenia, Huntington's Disease (HD), Parkinson's Disease, multiple sclerosis (MS), amyotrophic lateral sclerosis (ALS), Capgras (delusion) Syndrome, chronic fatigue syndrome, circadian rhythm sleep disorder, conduct disorder, communication/language disorders, Creutzfeldt-Jakob Disease (CJD), kuru, Gerstmann-Sträussler-Scheinker syndrome (GSS), fatal familial insomnia (FFI), cyclothymic disorder, acquired immune deficiency syndrome (AIDS), depression, addiction, Cushing's Syndrome (also called hyperadrenocorticism or hypercorticism), neoplasm (benign and malignant), stroke, diabetes (Type II), aneurysm, cardiovascular disease (including heart disease), Meniere's Disease, deafness, blindness, multiple system atrophy, Neiman Pick Disease, artherosclerosis, progressive supranuclear palsy, cancer, Tay-Sachs Disease, keratoconus, macular degeneration, inflammatory bowel disease (IBD), prostatis, male pattern baldness, obesity, paroxysmal nocturnal hemoglobinuria, thalassemia, Crohn's disease, Best disease, glaucoma, Gyrate atrophy of the choroid and retina, Charcot-Marie-Tooth syndrome, fibrodysplasia ossificans progressive, myotonic dystrophy, osteoarthritis, osteoporosis, arthritis, and rheumatoid arthritis.

Neurological Disorders

Compositions and methods of the invention are used to identify cells and subjects at risk of developing a neurological disorder or those cells and subjects who may have a predisposition for developing a neurological disorder. Moreover, the compositions and methods of the invention are used to differentiate neurological disorders for the purpose of diagnosing or prognosing a subject at risk of presenting or a subject who has been diagnosed with a neurological disorder. The compositions and methods of the invention are further used to monitor to progression of a neurological disorder or a treatment regime. Additionally, the compositions and methods of the invention are used to screen individuals for any genetic predisposition for presenting a neurological disorder himself/herself, or for producing a child having a neurological disorder.

The term "neurological disorder" includes any disorder that initially presents within the nervous system of an individual. Neurological disorders present with a variety of signs and symptoms including, but not limited to, psychological, mood, or behavioral changes; loss or decreased acuity of one or more senses (vision, hearing, touch); increased pain or burning sensations; lack of coordination or balance; loss of memory; loss of control over voluntary or involuntary movement; speech or balance; visual or auditory hallucinations; seizures; headaches; decreased movement; and ultimately, coma or death. Neurological disorders can result from genetic predisposition for developing the neurological disorder, one or more environmental factors that induce a the disorder to enhance the individual's genetic predisposition, or exposure of an individual to infectious agents such as a virus, a bacteria, a fungus, or a prion that induces the disorder or enhances the individual's genetic predisposition.

Exemplary neurological disorders include, but are not limited to, autism spectrum disorders (ASD), Angelman Syndrome, bipolar disorder, attention-deficit disorder (ADD), central auditory processing disorder (CAPD), cerebral palsy, Down Sydrome, expressive language disorder, Isopendric 15 (abbreviated idic(15)), Lanau-Kleffner Syndrome, neural tube defects, seizure disorders, epilepsy, Tourette Syndrome, traumatic brain injury (TBI), childhood disintegrative disorder, agnosias (visual, auditory, and somatosensory), anorexia nervosa disorder, acute stress disorder, adjustment disorder, bipolar disorder, body dysmorphic disorder, breathing-related sleep disorders, brief psychotic episode, bulimia nervosa, schizophrenia, Huntington's Disease (HD), multiple sclerosis (MS), amyotrophic lateral sclerosis (ALS), Capgras (delusion) Syndrome, chronic motor or vocal tic disorder, circadian rhythm sleep disorder, cluttering (speech disfluency), conduct disorder, communication/language disorders, Creutzfeldt-Jakob Disease (CJD), kuru, Gerstmann-Sträussler-Scheinker syndrome (GSS), fatal familial insomnia (FFI), depression, addiction, Fahr's Syndrome (or idiopathic basal ganglia calcification), migraine, neoplasm (benign and malignant), aphasia, paralysis, Bell's Palsy, cerebrovascular disease, encephalitis, hydrocephalis, microcephaly, Parkinson's Disease, trigeminal neuralgia, narcolepsy, muscular distrophy, Guillain-Barre Syndrome, neurofibromatosis, dyslexia, Rett Syndrome, Fragile X syndrome, adrenoleukodystrophy, ataxia telangiectasia, Cockayne syndrome, deafness, Duchenne muscular dystrophy, Gaucher disease, Lesch-Nyhan syndrome, maple syrup urine disease, Menkes syndrome, phenylketonuria, Prader-Willi syndrome, spinal muscular atrophy, spinocerebellar ataxia, tuberous sclerosis, Neimann-Pick syndrome, Refsum disease, Tay-Sachs disease, Charcot-Marie-Tooth syndrome, fibrodysplasia ossificans progressive, myotonic dystrophy, and Meniere's Disease.

Stem Cell Disorders

Compositions and methods of the invention are used to identify cells and subjects at risk of developing a "stem cell" disorder or those cells and subjects who may have a predisposition for developing a stem cell disorder. Moreover, the compositions and methods of the invention are used to differentiate stem cell disorders for the purpose of diagnosing or prognosing a subject at risk of presenting or a subject who has been diagnosed with a stem cell disorder. The compositions and methods of the invention are further used to monitor to progression of a stem cell disorder or a treatment regime. Additionally, the compositions and methods of the invention are used to screen individuals for any genetic predisposition for presenting a stem cell disorder himself/herself, or for producing a child having a stem cell disorder.

The term "stem cell disorder" includes any disorder that initially presents within a totipotent (or omnipotent), pluripotent, multipotent, oligopotent, or unipotent stem cell of an individual. Alternatively, or in addition, a stem cell disorder includes any disorder which can be treated or prevented by administering a composition including a stem cell to the individual. Stem cells are characterized by their ability to produce daughter cells, one of which will differentiate and the other of which will remain an undifferentiated stem cell. The potency of a stem cell relates to differentiation potential of the daughter cell that becomes committed to a particular cell fate. Specifically, the terms totipotent stem cell or omnipotent stem cell describe stem cells that can give rise to both embryonic stem cells or, alternatively, the stem cell can generate every type of cell in the human body. Pluripotent stem cells have a more restricted potential than totipotent stem cells, however, these stem cells can generate cells derived from any of the three germ layers (ectoderm, mesoderm, or endoderm). Multipotent stem cells have a more restricted potential than pluripotent stem cells, however, these stem cells can generate cells within a related lineage. Multipotent stem cells are often considered adult stem cells because they are found in, for instance, the adult brain (neural stem cells that give rise to neurons and all types of glia) and bones (bone marrow stem cells that give rise to all types of blood cells). Oligopotent stem cells have a more restricted potential than multipotent stem cells, however, these stem cells can generate a few related types of cells. For example, the corneal epithelium contains oliopotent stem cells that produce only corneal and conjunctival cells. Unipotent cells are the most restricted cell type because they can only reproduce their own cell type, however, they do maintain the ability to self-renew. Muscle stem cells are nonlimiting examples of unipotent stem cells.

Exemplary stem cell disorders include, but are not limited to, autism spectrum disorders (ASD), neural tube defects, seizure disorders, epilepsy, hearing loss, deafness, blindness, vision impairment, jaundice/kernicterus, cluttering (speech disfluency), agnosias (visual, auditory, and somatosensory), Huntington's Disease (HD), multiple sclerosis (MS), amyotrophic lateral sclerosis (ALS), chronic motor or vocal tic disorder, circadian rhythm sleep disorder, Alzheimer's Disease, dementia, senility, diabetes, Parkinson's Disease, muscular distrophy, Guillain-Barre Syndrome, sickle cell anemia or sickle cell disease, ataxia telagiectasia, Cockayne syndrome, DiGeorge syndrome, severe combined immunodeficiency, porphyria, paroxysmal nocturnal hemoglobinuria, thalassemia, familial Mediterranean fever, immunodeficiency with hyper-IgM, Charcot-Marie-Tooth syndrome, fibrodysplasia ossificans progressive, myotonic dystrophy, spinal muscular atrophy, spinocerebellar ataxia, and Gauchers Disease.

Kits

Kits include a composition containing at least one tag (as shown, for example, in Table 2), at least one bridge (as shown, for example, in Table 3), and a substance that is a either a volume excluder or a nuclease. Alternatively, kits include a composition containing one or more tags (as shown, for example, in Table 2), one or more bridges (as shown, for example, in Table 3), and a substance that is either a volume excluder or a nuclease. Tags are provided separately from the bridges. Alternatively, tags are provided in a mixture containing bridges because the degree of cross-hybridization between tag and bridge molecules is negligible. In certain embodiments, kits also include ligase. In certain embodiments, kits can include at least one tag, at least one bridge and a ligase. In these embodiments, kits can also include a volume excluder or a nuclease.

A nonlimiting example of a preferred ligase is the T4 DNA ligase, however, all ligases are encompassed by the invention. Ligases are often divided into classes referred to as EC 6.1 (form carbon-oxygen bonds), EC 6.2 (form carbon-oxygen bonds), EC 6.3 (form carbon-nitrogen bonds), EC 6.4 (form carbon-carbon bonds), EC 6.5 (form phosphoric ester bonds), and EC 6.6 (form nitrogen-metal bonds). Alternatively, or in addition, ligases are classified by the types of molecules they unite. RNA ligase and DNA ligase (types I-IV) are contemplated. Although the T4 DNA ligase is shown herein, other natural, recombinant, synthetic, or engineered ligases are encompassed by the invention.

A nonlimiting example of a preferred volume excluder is polyethylene glycol (PEG). Although PEG is shown herein, other polyether molecules are encompassed by the invention, including, but not limited to, poly(ethylene oxide) (PEO) and polyoxyethylene (POE), which vary by the size of the ethylene oxide polymer. Other natural, recombinant, synthetic, or engineered polymers with similar size, charge, and solubility to PEG are encompassed by the invention. Specifically, PEG is soluble in water, methanol, benzene, dichloromethane and is insoluble in diethyl ether and hexane.

A nonlimiting example of a nuclease is a DNA-specific exonuclease. Although the lambda exonuclease is shown herein, other natural, recombinant, synthetic, or engineered exonucleases are encompassed by the invention.

Kits further optionally contain a control RNA molecule. Control RNA molecules are preferably isolated and purified miRNA molecules to which a control bridge specifically hybridizes, and to which a specific tag is ligated. The corresponding control bridge and tag molecules are provided and labeled accordingly.

Kits also include instructions for handling the enclosed compositions and substances and protocols for performing singular or multiplexed denaturing, annealing, ligation, and/or purification reactions using the enclosed compositions and substances. Furthermore, the instructions provide guidance for preparing the resultant tagged RNA molecule(s) for detection using the NCOUNTER® Analysis System.

EXAMPLES

Example 1 mRNA Detection Kit Protocol

The NCOUNTER® miRNA Sample Preparation Kit provides reagents for ligating unique oligonuceotide tags onto miRNAs, allowing these short RNAs to be detected with great specificity and sensitivity in the standard NCOUNTER® gene expression assay. The miRNA tag ligation reaction can be performed in a background of total RNA.

Sample preparation involved a multiplexed annealing of the specific tags to their target miRNA, a ligation reaction, and an enzymatic purification to remove the unligated tags. Sequence specificity between each miRNA and its appropriate tag was ensured by careful, stepwise control of annealing and ligation temperatures. Control RNA included in the NCOUNTER® Human miRNA Sample Preparation Kit allowed the user to monitor the ligation efficiency and specificity through each step of the reaction. The total hands-on time for the sample preparation reaction was approximately 30 minutes, with an elapsed time of approximately 3 hours.

The NCOUNTER® miRNA expression assay was run on the NCOUNTER® Analysis system. The system was comprised of two instruments, the Prep Station used for post-hybridization processing, and the Digital Analyzer used for data collection.

After hybridization, excess probes were washed away using a two step magnetic beadbased purification on the NCOUNTER® Prep Station. Magnetic beads derivatized with short nucleic acid sequences that were complementary to the Capture Probe and the Reporter Probes were used sequentially. First, the hybridization mixture containing target/probe complexes was allowed to bind to magnetic beads complementary to sequences on the Capture Probe. Wash steps were performed to remove excess Reporter Probes and non-target cellular transcripts. After washing, the Capture Probes and target/probe complexes were eluted off the beads and are hybridized to magnetic beads complementary to sequences on the Reporter Probe. An additional wash was performed to remove excess Capture Probes. Finally, the purified target/probe complexes were eluted off the beads and immobilized on the cartridge for data collection.

Data Collection was carried out in the NCOUNTER® Digital Analyzer. Digital images were processed and the barcode counts were tabulated in a comma separated value (CSV) format.

Materials

TABLE 1.1

Materials and Reagents Required for miRNA Sample Preparation and miRNA Expression Assay

| Material | Manufacturer | Part Number |
|---|---|---|
| NCOUNTER® Human miRNA Expression Assay Kit | NanoString Technologies | GXA-MIR1-xx |
| NCOUNTER® Master Kit | NanoString Technologies | NAA-AKIT-xxx |
| QIAGEN MIRNEASY® Kit | QIAGEN (or equivalent total RNA purification kit) | |
| Disposable gloves | Various | |
| DEPC-treated (or RNAse-free) water | | |
| 100 ng total RNA per sample normalized to 33 ng/µL | | |

Thermocycler

The thermocycler used for the miRNA Sample Preparation Protocol had a heated lid, such as the MJ Research/BioRad models listed in Table 1.2. Other thermocyclers with heated lids are also expected to perform well, and the assay kit includes controls to verify proper performance. The thermocycler should be calibrated before using this assay.

TABLE 1.2

Instruments Required for miRNA Sample Preparation and miRNA Gene Expression Assay

| Material | Manufacturer | Part Number |
|---|---|---|
| NanoDrop ND-1000 (or equivalent spectrophotometer) | NanoDrop Technologies | N/A |
| Bioanalyzer 2100 | Agilent | G2940CA |
| Pipette for 0.5-10 µL | Rainin (or equivalent) | L-10 |
| Pipette for 2.0-20 µL | Rainin (or equivalent) | L-20 |
| Pipette for 20-200 µL | Rainin (or equivalent) | L-200 |
| Picofuge with strip-tube adaptor | Stratagene (or equivalent) | 400540 |
| DNA Engine Thermocycler or hybridization oven* | MJ Research/BioRad (or equivalent) | PTC-200G PTC-1148 PTC-0220G PTC-0221G PTC-0240G |
| nCounter Prep Station | NanoString Technologies | NCT-PREP-120 |
| nCounter Digital Analyzer | NanoString Technologies | NCT-DICA-120 |
| USB Drive | NanoString Technologies | N/A |

*Hybridization oven can be used for the miRNA Hybridization Protocol only. A thermocycler with a heated lid is required for the miRNA Sample Preparation Protocol.

The NCOUNTER® miRNA Preparation protocol used careful temperature control of all reaction steps. A thermocycler with a heated lid was used for this procedure. Before beginning, the thermocycler protocols were programmed as follows:

TABLE 1.3

Annealing Protocol

| Temperature | Time |
|---|---|
| 94° C. | 1 min |
| 65° C. | 2 min |
| 45° C. | 10 min |
| 48° C. | hold |
| Total Time | 13 min |

TABLE 1.4

Ligation Protocol

| Temperature | Time |
|---|---|
| 48° C. | 3 min |
| 47° C. | 3 min |
| 46° C. | 3 min |
| 45° C. | 5 min |
| 65° C. | 10 min |
| 4° C. | hold |
| Total Time | 24 min |

TABLE 1.5

Purification Protocol

| Temperature | Time |
|---|---|
| 37° C. | 2 hours |
| 70° C. | 10 min |
| 4° C. | hold |
| Total Time | 2 hours 10 min | mRNA Sample Preparation Protocol

All experiments were designed in sets of twelve assays. The protocol below is for one set of 12 assays. All reagents are supplied in 12 reaction aliquots.

1. RNA samples were normalized to 33 ng/μL using DEPC (or RNAse-free) H20.
2. A 1:500 dilution of the miRNA Assay Controls was prepared. 499 μL DEPC H$_2$O was added to 1 μL of the miRNA Assay Controls in a sterile microcentrifuge tube. The tube was mixed by vortexing, briefly spun down and stored on ice.
3. An annealing master mix was prepared by combining 13 μL, of Annealing Buffer, 26 μL, of nCounter® miRNA Tag Reagent and 6.5 μL, of the 1:500 miRNA Assay Controls dilution prepared in Step 2. This was mixed well by pipetting up and down.
4. 3.5 μL of the annealing master mix was aliquoted into each tube.
5. 3 μL (100 ng) of RNA sample was added to each tube. Tubes were capped, flicked gently to mix and spun down.
6. The strip was placed in the thermocycler and the Annealing Protocol was initiated.
7. 19.5 μL PEG was combined with 13 μL Ligation Buffer to prepare a ligation master mix.
8. Following completion of the Annealing Protocol, when the thermocycler reached 48° C., 2.5 μL of the ligation master mix was added to each tube. (The thermocycler was left on so that it was maintained at 48° C. for Step 9 and Step 10). The tubes were flicked gently to mix and spun down.
9. The tubes were returned to the 48° C. thermocycler, the lid was closed, and the tubes were incubated at 48° C. for 5 min.
10. The thermocycler was opened, the caps were carefully removed from tubes, leaving the tubes in place in the heat block, and 1.0 μL of Ligase was added directly to each tube while they were incubated at 48° C. The pipette tip was checked to make certain all of the ligase was added to the reaction. There was no need to mix.

NOTE: PEG is viscous was pipetted slowly to ensure accurate transfer of volume into the mix. It was mixed well by pipetting up and down.

NOTE: For Step 10, the tubes were not removed from the thermocycler, maintaining the temperature of the tubes at 48° C.

11. Immediately after addition of Ligase to the final tube, the tubes were recapped and left in heat block. The thermocycler was closed and the Ligation Protocol was initiated.
12. After completion of Ligation Protocol, 1 μL Ligation Clean-Up Enzyme was added to each reaction. The tubes were removed from the heat block for this step. The tubes were flicked gently to mix and spun down.
13. The tubes were returned to the thermocycler and the Purification Protocol was initiated.
14. After completion of Purification Protocol, 40 μL DEPC was added (or RNAse-free) H$_2$O to each sample. This was mixed well and spun down. (If necessary, at this stage the purified sample preparation reactions were stored at −20° C. for up to several weeks.) Samples were denatured (Step 5 of miRNA Hybridization Protocol) before proceeding to the hybridization protocol.)

Hybridization Protocol

The final hybridization reaction contained the following components: 10 μL Reporter CodeSet, 10 μL hybridization buffer, a 5 μL aliquot from the miRNA Sample Preparation Protocol, and 5 μL Capture ProbeSet.

1. Aliquots of both the Reporter CodeSet and Capture ProbeSet reagent were removed from the freezer and thawed on ice. The aliquots were inverted several times to mix well. The reagent was briefly spun down at <1000 rpm.
2. A master mix was created containing 130 μL of the Reporter CodeSet and 130 μL of hybridization buffer by adding the hybridization buffer to the tube containing the Reporter CodeSet. The master mix was inverted to mix and spun down.
3. Tubes were labeled.
4. 20 μL of master mix was added to each of the 12 tubes.
5. Samples were denatured from the miRNA sample prep protocol at 85° C. for 5 minutes and quick-cooled on ice. A 5 μL aliquot from the miRNA Sample Preparation Protocol was added to each tube. During the setup of the assay, mixing was done by flicking or inverting the tubes.
6. The thermocycler was pre-heated to 65° C. and then programmed using 30 μL volume, calculated temperature, heated lid and "forever" time setting.
7. 5 μL of Capture ProbeSet was added to each tube immediately before placing at 65° C. Tubes were capped and the reagents mixed by inverting the strip tubes several times and flicking to ensure complete mixing. The tubes were briefly spun down at <1000 rpm and immediately the tubes were placed in the 65° C. thermocycler.
8. Hybridization assays were incubated for at least 12 hours. Hybridizations were left at 65° C. until ready for processing. Maximum hybridization time did not exceed 30 hours.
9. Once removed from the thermocycler, we proceeded immediately to post-hybridization processing with the NCOUNTER® Prep Station.

Example 2

Multiplexed NCOUNTER® miRNA Expression Assay Kits Distinguish Individual Species of miRNAs with High Specificity A multiplexed set of assays for 55 different miRNAs was run on individual synthetic miRNA targets present at 3 pM in the ligation, and 300 fM in the final hybridization reaction (Table 5). Representative data for 10 targets and the corresponding 10 assays (a subset of the 55 multiplexed assays) are shown. The data is in counts per 600 fields-of-view. Each assay within the multiplexed set shows a strong specificity for the miRNA target it is designed to detect.

TABLE 5

Data for Example 2.

| miRNA assay | miRNA target | | | | | | | | | |
|---|---|---|---|---|---|---|---|---|---|---|
| | miR-15a | miR-15b | miR-25 | miR-92a | miR-92b | miR-122 | miR-133a | miR-143 | miR-195 | miR-206 |
| miR-15a | 16143 | 1 | 2 | 1 | 1 | 1 | 2 | 2 | 2 | 3 |
| miR-15b | 1 | 14659 | 2 | 0 | 1 | 3 | 2 | 3 | 3 | 5 |
| miR-25 | 0 | 0 | 8066 | 1 | 0 | 1 | 1 | 2 | 3 | 41 |
| miR-92a | 1 | 2 | 4 | 15558 | 2 | 2 | 2 | 2 | 3 | 3 |
| miR-92b | 0 | 6 | 0 | 20 | 20145 | 0 | 1 | 1 | 0 | 2 |
| miR-122 | 0 | 2 | 1 | 13 | 10 | 12324 | 2 | 1 | 1 | 1 |
| miR-133a | 0 | 0 | 1 | 2 | 4 | 12 | 16217 | 2 | 3 | 1 |
| miR-143 | 0 | 0 | 1 | 1 | 9 | 3 | 5 | 13519 | 3 | 2 |
| miR-195 | 0 | 0 | 2 | 0 | 1 | 1 | 2 | 1 | 20814 | 2 |
| miR-206 | 0 | 0 | 1 | 1 | 1 | 3 | 2 | 2 | 25 | 20754 |

Example 3

Multiplexed NCOUNTER® Assays Kits Reveal MiRNA Expression Levels in Different Tissue Types MiRNAs can be expressed at similar levels in a range of tissues, but many also exhibit differential expression in different tissue types. In these experiments, multiplexed NCOUNTER® miRNA Expression Assays for 619 human miRNAs were run on total RNA purified from various human tissues (Ambion), including lung, skeletal muscle, colon and heart, and the data were compared in pairwise sets. Hundreds of microRNAs were specifically detected in each sample. In FIGS. 5A-D, the data points that fall on the diagonal are those miRNAs which were expressed at similar levels in both tissues. Those that fall outside of the diagonal represent miRNAs which were differentially regulated in the two tissue types. These results show the ability of the NCOUNTER® miRNA Expression Assay Kit in a highly multiplexed context to measure the differential expression of hundreds of small RNAs.

Figure 6A:
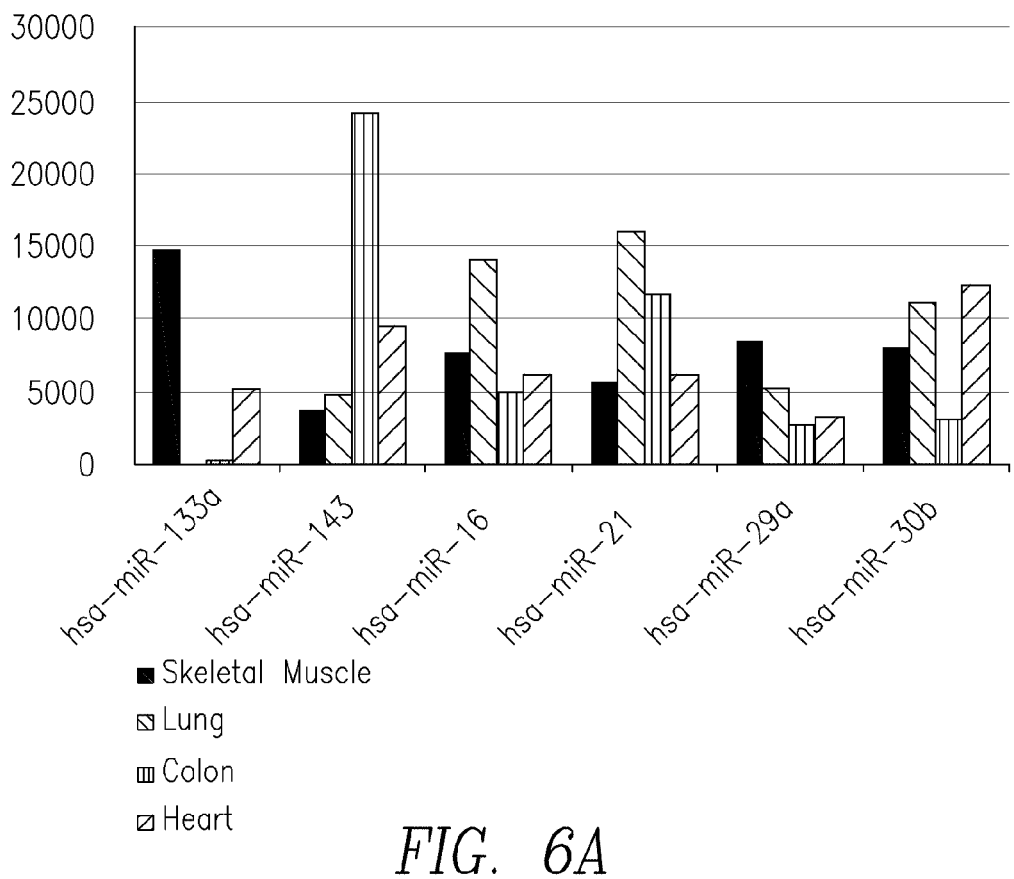
FIG. 6A is a graph depicting the expression levels of human miRNAs miR-133a, miR-143, miR-16, miR-21, miR-29a, and miR-30 in total RNA isolated from skeletal muscle, lung, colon, and heart tissue. Samples were measured using the NCOUNTER® miRNA Expression Assay Kit.
Figure 6B:
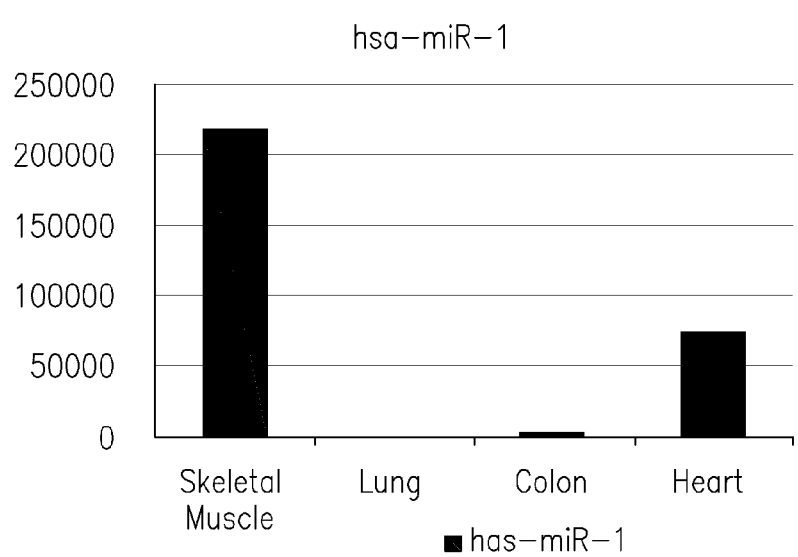
FIG. 6B is a graph depicting the expression levels of human miRNA miR-1 in total RNA isolated from skeletal muscle, lung, colon, and heart tissue. Samples were measured using the NCOUNTER® miRNA Expression Assay Kit.

FIGS. 6A-B, taken from the same data sets, highlight the differential expression of several specific miRNAs in the four tissue types. In FIG. 6A, the different expression levels of six human miRNAs, miR-133a, -143, -16, -21, -29a and -30b, can be seen to range from approximately 0 to 25,000 counts, while FIG. 6B shows the muscle-specific expression of human miR-1, which is essentially undetected in lung and colon tissue, but gives over 200,000 counts in skeletal muscle and 75,000 counts in heart tissue. These data demonstrate the ability of the NCOUNTER® miRNA Expression Assay Kit in a highly multiplexed context to measure differences in the specific expression of a given miRNA over a large range of expression levels.

Example 4

The NCOUNTER® miRNA Expression Assay Kit Identifies RNAs in Clinical Samples

Figure 7:
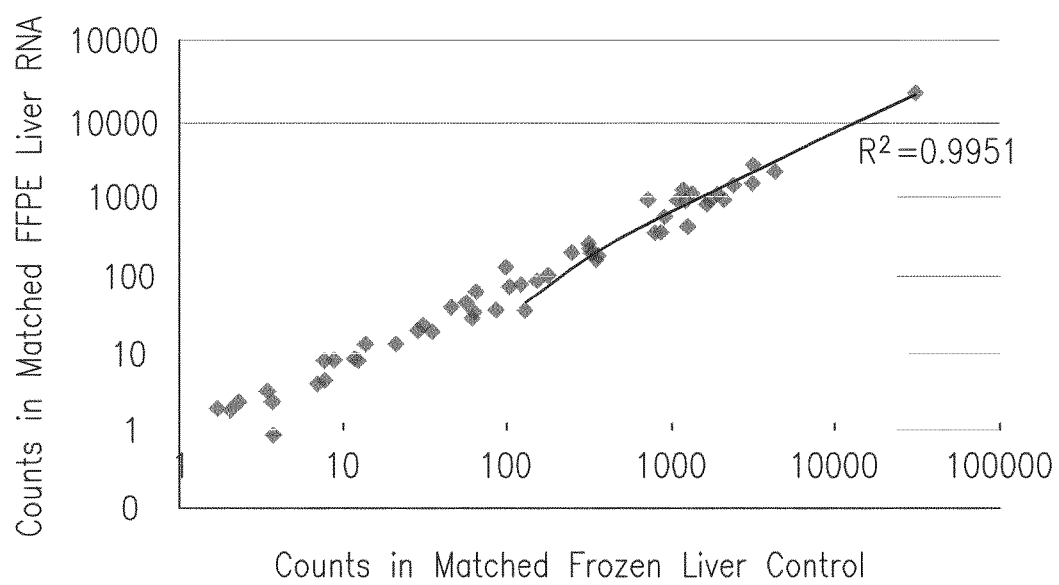
FIG. 7 is a graph depicting the results of multiplexed NCOUNTER® miRNA Expression Assays for 55 human miRNAs run on 100 ng of total RNA purified from either formalin-fixed, paraffin-embedded (FFPE) or frozen human liver samples collected from the same tissue source. The results are displayed as counts in matched FFPE Liver RNA versus counts in matched frozen liver control.

The ability to detect RNAs in a variety of sample types is an important feature in gene expression assays. Of particular interest in the field of small RNAs is the ability to measure their expression levels in clinical samples, where they may provide prognostic, diagnostic or therapeutic information. Clinical tissue samples are frequently preserved as formalin-fixed, paraffin-embedded (FFPE) samples, leading to modifications of the target RNA structure. Not all gene expression assays are compatible with RNA isolated from FFPE samples. Total RNA was isolated from FFPE samples using a miREasy FFPEKit (Qiagen, Gaithersburg, Md.) following the manufacturer's instructions, and data obtained in the NCOUNTER® miRNA Expression Assay Kit using these samples was compared to the data obtained using total RNA isolated from the same tissue stored as a frozen sample. The results of these experiments demonstrate that the NCOUNTER® miRNA Expression Assay Kit is able to detect small RNAs in FFPE samples with the same specificity and sensitivity as in total RNA. A representative data set shown in FIG. 7 demonstrates an extremely high correlation between the data from the two sample types, with an $R^2$ value of greater than 0.99.

Example 5

The NCOUNTER® miRNA Expression Assay Kit Provides a Multiplexed Format

Figure 8:
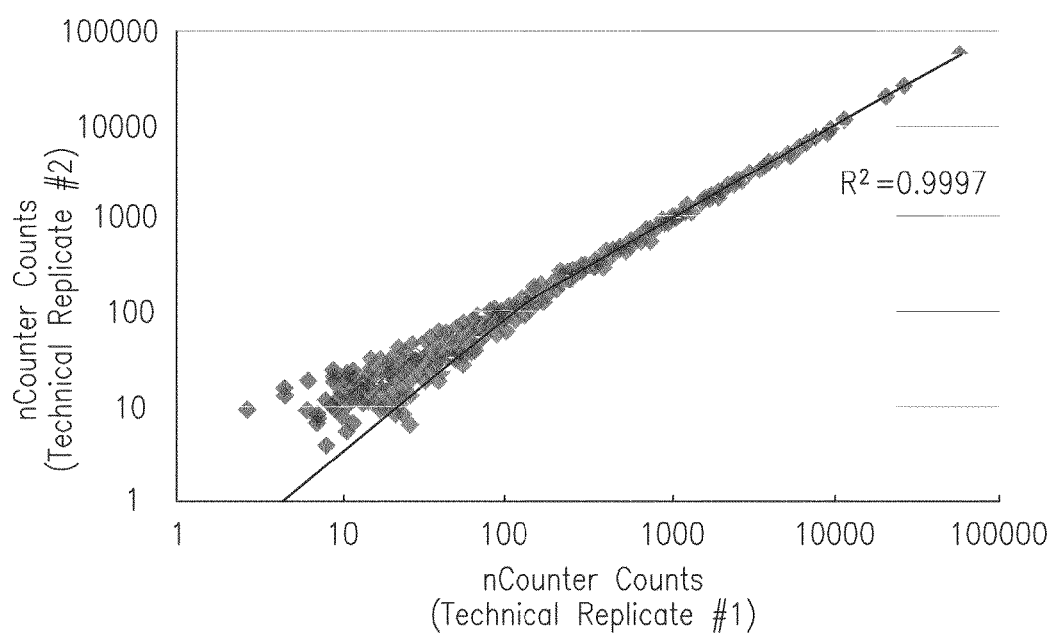
FIG. 8 is a graph depicting the correlation of two technical replicates in which multiplexed NCOUNTER® miRNA Expression Assays for 676 human miRNAs were run on 100 ng of human brain total RNA. The data are displayed as NCOUNTER® counts (Technical Replicate #2) versus NCOUNTER® counts (Technical Replicate #1).

NCOUNTER® miRNA Expression Assay Kits generate reproducible data in a multiplexed format. FIG. 8 shows the correlation of the data from two technical replicates in which multiplexed assays for 676 human miRNAs were run on 100 ng of Human Brain Reference total RNA (Stratagene, LaJolla, Calif.). The data from the two replicate experiments demonstrate an extremely high correlation, with an $R^2$ value of greater than 0.999.

Example 6

Figure 9A:
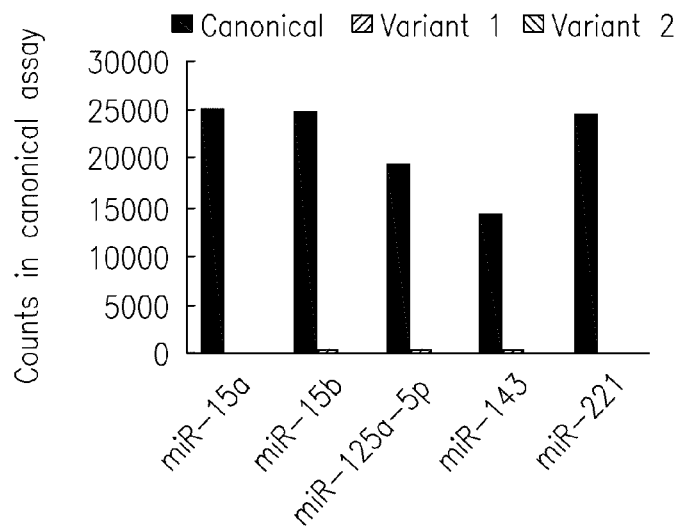
FIG. 9A is a series of graphs depicting mixtures of five canonical (left), variant 1 (center), or variant 2 (right) synthetic miRNAs assayed with the canonical and variant bridge pools in multiplexed NCOUNTER® miRNA Expression Assays. The graphs display the counts resulting when each of the three mixtures was assayed the canonical (black bars), variant 1 (white bars), and variant 2 (gray bars) bridge pools.
Figure 9A:
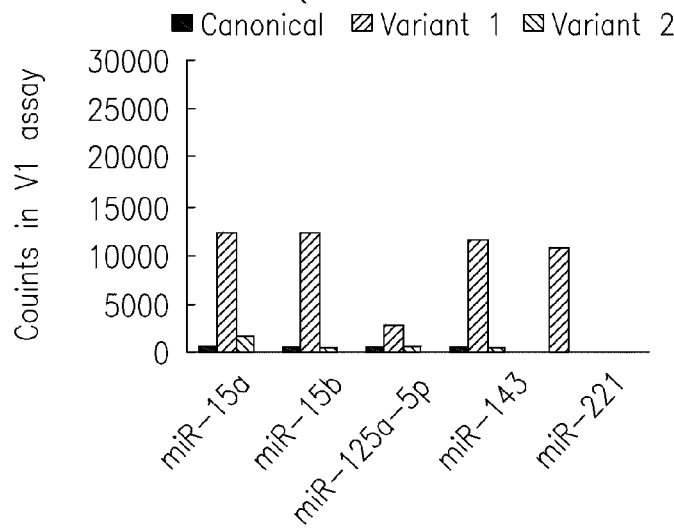
Figure 9A:
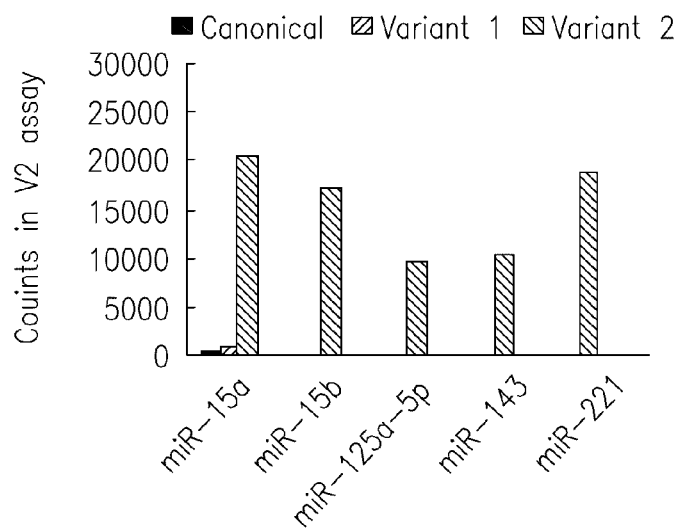
Figure 9B:
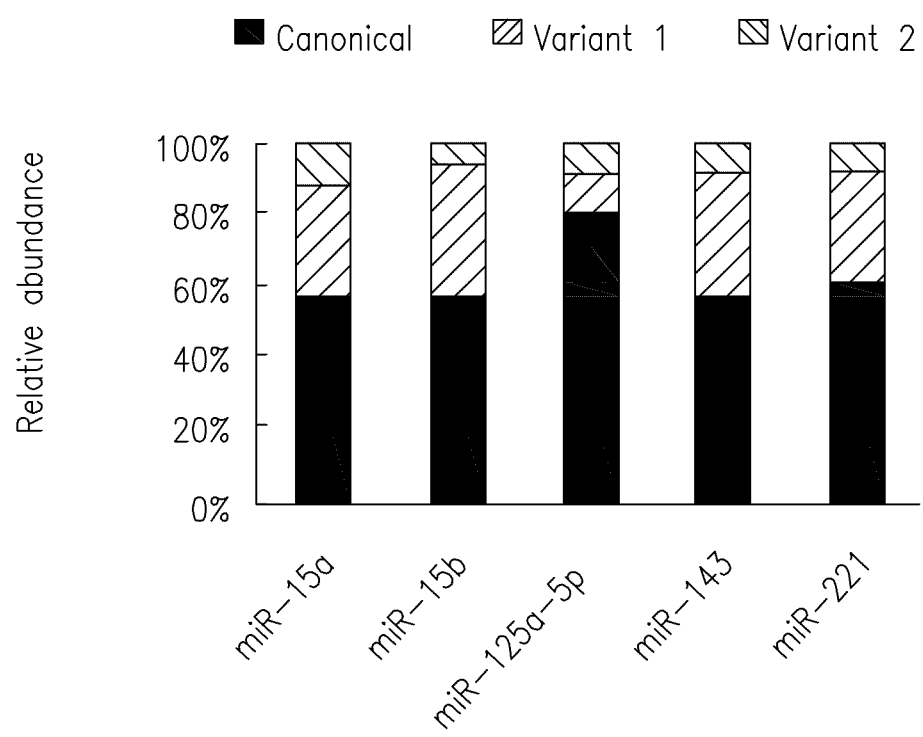
FIG. 9B is a graph depicting results from NCOUNTER® miRNA Expression Assays used to measure a mixture containing 60% canonical (black), 30% variant 1 (white), and 10% variant 2 (gray) for each of 5 miRNAs. The relative abundance of each species measured in the assay is indicated as a percentage of total signal for each miRNA.

The NCOUNTER miRNA Expression Assay Kit Enables Profiling of 3' Sequence Variants of miRNAs In order to study 3' sequence variants of miRNAs, NCOUNTER® miRNA Expression Assay bridges may be created that direct the tagging of the variant miRNAs. Here we measured the two most common 3' variants (arbitrarily designated variant 1 and variant 2) for each miRNA of interest. Each sample was split into three and assayed separately with a canonical bridge pool, the variant 1 bridge pool, and the variant 2 bridge pool. In this experiment, the bridges directed the variants to the same tag as the canonical sequence, and thus had to be detected in separate assays. It is also possible to design bridges which direct each variant to a unique tag, allowing for the detection of all variants in the same assay. Specificity of the platform was demonstrated by assaying mixtures of five canonical, variant 1, or variant 2 synthetic miRNAs with each of the three bridge pools. We found that each bridge pool reliably distinguished the miRNA species of interest (FIG. 9A), with minimal background detection of the other variants. We also assayed mixtures of synthetic miRNAs containing 60% canonical miRNA, 30% variant 1, and 10% variant 2 and found that, in general, the correct ratio of canonical to variant miRNAs could be distinguished (FIG. 9B). These results demonstrate that the NCOUNTER® miRNA Expression Assay provides a robust platform by which to investigate the expression of 3' sequence variants of miRNAs.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A composition comprising at least two tripartite complexes, each tripartite complex comprising:
(a) a tag molecule, wherein the tag molecule comprises a first DNA sequence and a plurality of reporter attachment regions and wherein the first DNA sequence comprises a DNA sequence having no greater than 85% identity across 35-50 bases with a maximum continuous homology of 15 bases or less to any known genomic DNA or RNA transcribed from a genome;
(b) one or more reporter molecules each non-covalently attached to one of the plurality of reporter attachment regions of the tag molecule, wherein the one or more reporter molecules together produces a code comprising an ordered series of colored fluorescent spots that identifies a target RNA molecule; and
(c) a bridge molecule, wherein the bridge molecule comprises a second DNA sequence that is complementary to the target RNA molecule and a third DNA sequence that is complementary to the first DNA sequence of the tag molecule;

wherein a first tripartite complex identifies a first target RNA molecule and comprises a bridge molecule that is complementary to the first target RNA molecule;

wherein an at least second tripartite complex identifies an at least second target RNA molecule and comprises a bridge molecule that is complementary to the at least second target RNA molecule; and wherein the first and the at least second target RNA molecules are different.

2. The composition of claim 1, wherein the second DNA sequence and the third DNA sequences of each bridge molecule are contiguous.

3. The composition of claim 1, wherein the first target RNA molecule or the at least second target RNA molecules comprises a non-coding RNA.

4. The composition of claim 3, wherein the non-coding RNA is a transfer RNA (tRNA), a small nucleolar RNA (snoRNA), a microRNA (miRNA), a short interfering RNA (siRNA), a short hairpin RNA (shRNA), a repeat associated small interfering RNA (rasiRNA), or a piwi-interacting RNA (piRNA).

5. The composition of claim 3, wherein the non-coding RNA is a miRNA.

6. The composition of claim 1, wherein Bathe second DNA sequence of each bridge molecule and the target RNA molecule of each tripartite complex form a DNA/RNA heteroduplex having a melting temperature of between 37-95° C.

7. The composition of claim 1, wherein the second DNA sequence of each bridge molecule and the target RNA molecule of each tripartite complex form a DNA/RNA heteroduplex having a melting temperature of between 44-53° C.

8. The composition of claim 1, wherein the third DNA sequence of the each bridge molecule and the first DNA sequence of each tag molecule form a DNA/DNA duplex having a melting temperature of between 37-95° C.

9. The composition of claim 1, wherein the third DNA sequence of each bridge molecule and the first DNA sequence of each tag molecule form a DNA/DNA duplex having a melting temperature of between 44-53° C.

10. The composition of claim 1, wherein the second DNA sequence and the third DNA sequence of each bridge molecule form nucleic acid duplexes having substantially the same melting temperature.

11. The composition of claim 1, wherein the third DNA sequence of each bridge molecule comprises a DNA sequence having no greater than 85% identity across 35-50 bases with a maximum continuous homology of 15 bases or less to any known genomic DNA.

12. The composition of claim 1, wherein the target RNA molecule or the tag molecule of each tripartite complex contains a sequence that specifically hybridizes to the bridge molecule of the tripartite complex with complete complementarity.

13. The composition of claim 1, wherein the target RNA molecule or the tag molecule of each tripartite complex contains a sequence that specifically hybridizes to the bridge molecule of the tripartite complex with partial complementarity.

14. The composition of claim 1, wherein when each of said tripartite complex in the composition is complexed with its target RNA molecule, said target RNA molecule can be ligated to said tag molecule.

15. The composition of claim 1, wherein at least one of said tripartite complexes comprises or is complementary to one or more of SEQ ID NO: 1 to SEQ ID NO: 35.

* * * * *